US010758213B2

(12) United States Patent
McWeeney et al.

(10) Patent No.: US 10,758,213 B2
(45) Date of Patent: Sep. 1, 2020

(54) EXCHANGEABLE CORE BIOPSY NEEDLE

(71) Applicant: COVIDIEN LP, Mansfield, MA (US)

(72) Inventors: John O. McWeeney, Brighton, MA (US); Eugene Campbell, Natick, MA (US); Bora Gumustop, Slingerlands, NY (US)

(73) Assignee: Covidien LP, Mansfield, MA (US)

( * ) Notice: Subject to any disclaimer, the term of this patent is extended or adjusted under 35 U.S.C. 154(b) by 377 days.

(21) Appl. No.: 15/816,552

(22) Filed: Nov. 17, 2017

(65) Prior Publication Data

US 2018/0070930 A1    Mar. 15, 2018

Related U.S. Application Data

(63) Continuation of application No. 14/595,392, filed on Jan. 13, 2015, now Pat. No. 9,844,362.

(51) Int. Cl.
*A61B 5/00* (2006.01)
*A61B 10/02* (2006.01)
*A61B 8/08* (2006.01)

(52) U.S. Cl.
CPC ........ *A61B 10/0266* (2013.01); *A61B 8/0841* (2013.01); *A61B 10/0233* (2013.01)

(58) Field of Classification Search
CPC ............ A61B 10/0233; A61B 10/0266; A61B 8/0841; A61B 17/3417; A61M 5/3286
See application file for complete search history.

(56) References Cited

U.S. PATENT DOCUMENTS 4,708,147 A    11/1987  Haaga
4,850,354 A    7/1989   Mcgurk-Burleson
4,983,179 A    1/1991   Sjostrom
5,313,958 A    5/1994   Bauer
5,536,259 A    7/1996   Utterberg
5,615,690 A    4/1997   Giurtino
(Continued)

FOREIGN PATENT DOCUMENTS

EP    0221007 A1    5/1987
EP    2520237 A1    11/2012
(Continued)

OTHER PUBLICATIONS

Creganna Needle Brochure, published Jan. 16, 2008.
(Continued)

*Primary Examiner* — Max F Hindenburg
(74) *Attorney, Agent, or Firm* — Holland & Hart LLP

(57) ABSTRACT

The present disclosure generally relates to a biopsy needle configured to maximize tissue sampling yield and collect a unit of sampled tissue. The biopsy needle includes an elongate tubular body comprising a lumen extending therethrough from a proximal open end to a distal open end of the body. The distal end includes first and second tip portions extending therefrom and formed on opposing sides of the needle body. The first tip portion generally extends further from the distal end than the second tip portion, resembling a staggered configuration, resulting in an increased surface area of multiple cutting edges formed between the first and second tip portions on either side of the needle body. Additionally, each of the tip portion defines a penetrating point configured to pierce the tissue to be sampled and direct sampled tissue towards the lumen of the body to be excised by the cutting edges.

10 Claims, 13 Drawing Sheets

(56) References Cited

U.S. PATENT DOCUMENTS

| | | |
|---|---|---|
| 5,733,266 A | 3/1998 | Gravlee |
| 5,746,724 A | 5/1998 | Powles |
| 5,752,923 A | 5/1998 | Terwilliger |
| 5,752,942 A | 5/1998 | Doyle |
| 5,810,788 A | 9/1998 | Racz |
| 5,817,033 A | 10/1998 | Desantis |
| 5,868,684 A | 2/1999 | Arig |
| 5,971,939 A | 2/1999 | Desantis |
| 5,968,022 A | 10/1999 | Saito |
| 6,009,933 A | 1/2000 | Doyle |
| 6,027,458 A | 2/2000 | Janssens |
| 6,027,514 A | 2/2000 | Stine |
| 6,213,989 B1 | 4/2001 | Utterberg |
| 6,315,737 B1 | 11/2001 | Skinner |
| 6,702,790 B1 | 3/2004 | Chauncey |
| 6,752,769 B2 | 6/2004 | Alberico |
| 6,890,308 B2 | 5/2005 | Islam |
| RE38,776 E | 8/2005 | Bauer |
| 6,945,964 B2 | 9/2005 | Hilderbrand |
| 7,008,381 B2 | 3/2006 | Janssens |
| 7,018,343 B2 | 3/2006 | Plishka |
| 7,070,583 B1 | 7/2006 | Higuchi |
| 7,320,683 B2 | 1/2008 | Prias |
| 7,455,645 B2 | 11/2008 | Goldenberg |
| 7,468,055 B2 | 12/2008 | Prais |
| 7,470,249 B2 | 12/2008 | Junger |
| 7,591,807 B2 | 9/2009 | Villete |
| 7,645,268 B2 | 1/2010 | Mickley |
| 7,731,667 B2 | 6/2010 | Goldenberg |
| 8,114,110 B2 | 2/2012 | Bednarek |
| D657,461 S | 4/2012 | Schembre |
| 8,317,727 B2 | 11/2012 | Peliks |
| 8,328,772 B2 | 12/2012 | Kinast |
| 8,449,478 B2 | 5/2013 | Lee |
| D690,009 S | 9/2013 | Schembre |
| 8,568,422 B2 | 10/2013 | Morlet |
| 8,622,925 B2 | 1/2014 | Dunn |
| 8,728,005 B2 | 5/2014 | Mcclellan |
| 8,771,199 B2 | 7/2014 | Theobald |
| 2006/0030785 A1 | 2/2006 | Field |
| 2009/0018468 A1 | 1/2009 | Janssens |
| 2011/0224577 A1 | 9/2011 | Park |
| 2012/0001162 A1 | 1/2012 | Nagamatsu et al. |
| 2012/0116248 A1 | 5/2012 | Mcweeney |
| 2012/0130274 A1 | 5/2012 | Persat |
| 2012/0157880 A1 | 6/2012 | Haselby |
| 2012/0165832 A1 | 6/2012 | Oostman, Jr. |
| 2012/0245486 A1 | 9/2012 | Melchiorri |
| 2012/0253228 A1 | 10/2012 | Schembre |
| 2012/0289985 A1 | 11/2012 | Motai |
| 2013/0041286 A1 | 2/2013 | Theobald |
| 2013/0102925 A1 | 4/2013 | McGhie |
| 2013/0131547 A1 | 5/2013 | Hardert |
| 2013/0131548 A1 | 5/2013 | McGhie |
| 2015/0313580 A1 | 11/2015 | Dejima |

FOREIGN PATENT DOCUMENTS

| | | |
|---|---|---|
| EP | 2982309 A1 | 2/2016 |
| JP | H07100140 A | 4/1995 |
| WO | 9204062 | 3/1992 |
| WO | 9508291 A1 | 3/1995 |
| WO | 972070 A1 | 7/1997 |
| WO | 2011126963 A2 | 10/2011 |
| WO | 2013074653 A1 | 5/2013 |
| WO | 2014112518 A1 | 7/2014 |

OTHER PUBLICATIONS

Chinese Office Action dated Feb. 6, 2016, for CN App. Model No. 201520562976,8 from the Chinese Patent Office.
EP extended European Search Report dated Jan. 11, 2015 in European application No. 15178119.2 from the European Patent Office.
EP extended European Search Report for Application No. 15178995.5 dated May 23, 2016, from the European Patent Office.
EP partial European search report for Application 15178995.5 dated Feb. 3, 2016 from the European Patent Office.
EP extended European search report for Application No. 15191407.4 dated Jun. 3, 2016 from the European Patent Office.
EP extended European search report for Application No. 15178119.2 dated Jan. 11, 2016 from the European Patent Office.
Notice of Reasons for Rejection for Japanese Patent Application No. 2015-148633, dated Aug. 3, 2016, from the Japanese Patent Office.
Notice of Reasons for Rejection for Japanese Patent Application No. 2015-146692, dated Aug. 3, 2016, from the Japanese Patent Office.

SECTIONAL VIEW X-X

SECTIONAL VIEW Y-Y

EXCHANGEABLE CORE BIOPSY NEEDLE

CROSS-REFERENCE TO RELATED APPLICATIONS

This application is a continuation of Ser. No. 14/595,392, filed Jan. 13, 2015, entitled, "EXCHANGEABLE CORE BIOPSY NEEDLE," which is incorporated by reference in its entirety for all purposes.

FIELD OF THE INVENTION

The present disclosure generally relates to biopsy devices, and, more particularly, to a biopsy needle configured for collecting tissue, fluid, and/or cell samples in conjunction with minimally-invasive procedures, such as endoscopic biopsy procedures.

BACKGROUND

In the practice of medical diagnostics, it is often necessary to perform a biopsy to remove a sample of a patient's tissue or fluid for pathological study. For example, biopsies can be useful in diagnosing various forms of cancer and other diseases affecting a localized area of tissue. Biopsy procedures may be used to take tissue and/or fluid samples from muscles, bones and organs, such as the liver or lungs. In some instances, a biopsy sample may be obtained by invasive surgical procedures. However, minimally invasive biopsy procedures are often preferred, such as fine needle aspiration and fine needle biopsy because such procedures are less traumatic to the patient.

Both fine needle aspiration (FNA) and fine needle biopsy (FNB) procedures generally include the use of a biopsy needle for collecting the target sample. FIGS. 1 and 2 are provided to illustrate one embodiment of a biopsy needle 100 currently available for use in biopsy procedures. As shown, the needle 100 includes a shaft 102 portion extending from a proximal end (not shown) to a distal cutting end 104 of the needle 100. The distal cutting end 104 includes a beveled leading end 106 resulting in a relatively sharp tip portion 110 used for puncturing the tissue to be sampled. The distal cutting end 104 of the needle 100 may be configured to cut and/or scrape target tissue to collect cells, tissue, or fragments. To sample the target area, the biopsy needle 100 may be guided to the tissue to be sampled through an instrument positioned in a patient. The instrument may be used with an endoscope, conduit and/or medical device insertion instrument. As shown, the needle 100 may be positioned within a sheath 108 of an endoscopic device, for example, such that the biopsy needle 100 may be retracted and extended from the sheath 108.

Upon contacting the tissue to be sampled (via the distal cutting end 104), the tissue sample may be collected within a lumen 112 of the shaft 102. In some devices, the needle 100 may extend from the sheath 108 and into the target tissue via a spring mechanism (not shown), such that the spring applies a force to the needle 100 and subsequently forces the distal cutting end 104 into the target tissue. Upon making contact with the target tissue, the distal cutting end 104 may separate a portion of the tissue from the surrounding tissue and collect the separated tissue within the lumen 112, which may result in a "core" sample (e.g., a number of intact adjacent cells held together in similar form to their native location). Additionally, or alternatively, suction may be applied to the proximal end of the needle 100 so as to aspirate the sample (e.g., cells, tissue, etc.) through the distal cutting end 104 of the needle 100 and into the lumen 112.

Generally, the goal of FNA and/or FNB is to acquire sufficient tissue to allow a diagnosis to be made. Currently, different needle tip configurations are used to collect different sample types (e.g., intact multi-cell samples useful for histology, cells and fragments useful for cytology, etc.). However, many existing biopsy needles are inefficient when collecting samples. For example, some needles use only about half or less of their inner diameter of the lumen to obtain tissue. Further, some current needle tip designs generally result in tearing of target tissue, which may result in a less than ideal core sample and unnecessary trauma to the surrounding tissue, which may cause further complications to the patient (e.g., internal bleeding, bruising, etc.) requiring further treatment.

Some devices that obtain a full cylinder or "full core" of tissue have difficulty in withdrawing tissue and/or in maintaining the physical state of the tissue so as to provide an accurate assessment of tissue condition. For example, some needles rely on scoring and/or mashing techniques during tissue collection, which may result in a damaged tissue sample. Depending on the diagnostics, physical characteristics of tissue, such as placement or orientation of cells or tissue, may be as important or more important than the chemical or biological characteristics (e.g. presence of malignant cells or by-products).

Furthermore, current needle tip designs may be insufficient for biopsy of certain types of tissue. For example, some lesions are particularly fibrous (e.g., pancreatic lesions) and are difficult to penetrate and obtain a suitable biopsy therefrom. Some bevel designs, such as the standard beveled cutting end of needle 100, may initially pierce a portion of the target lesion, but may then deflect off of or drift from the target lesion due to the inadequate tip design and/or inability to fully penetrate the lesion, which results in a poor tissue sample, and may even lead to damage to surrounding tissues or vital organs. Additionally, current bevel designs may merely shear off a portion of the target tissue and fail to collect some, or even all, of the sampled tissue within the lumen of the needle due to inadequate tip design.

SUMMARY

The present disclosure provides a biopsy needle configured to maximize tissue sampling yield and further ensure collection of a cohesive unit of sampled tissue, thereby overcoming the drawbacks of current biopsy needles, which either provide an insufficient amount of a sample for analysis and/or damage a sample during the collection process. The biopsy needle of the present disclosure is able to overcome the drawbacks of current needles by providing a distinct distal cutting end configured to collect a full core of tissue sample and keep the full core intact. More specifically, the distal end includes at least a first tip portion and a second tip portion that radially oppose one another on either side of the needle body. The first tip portion is longer than the second tip portion, resulting in an increase in the surface area of one or more cutting edged extending between the first and second tip portions on either side of the needle body, particularly when compared to the cutting surface of a beveled leading distal end of a conventional biopsy needle (e.g., see the needle of FIGS. 1 and 2). Additionally, because the first tip portion generally extends further than the second tip portion, the first tip portion is configured to initially pierce the tissue to be sampled with little or no resistance and further guide the sample tissue into the lumen of the biopsy needle. As the tissue is guided toward the lumen, second tip portion is further configured to capture and lead additional tissue towards the lumen to be excised by the cutting edge upon contact therewith. By increasing the effective cutting surface area and having the staggered configuration of first and second tip portions, the biopsy needle of the present disclosure is able to guide tissue into the lumen in a controlled manner and maximize the amount of tissue harvested, particularly upon aspiration.

In certain aspects, the present disclosure provides a biopsy needle that generally includes an elongate tubular body having a longitudinal axis and has a lumen extending therethrough from a proximal open end to a distal open end of the body. The distal end includes first and second tip portions extending therefrom. The first tip portion generally extends further from the distal end than the second tip portion, resembling a staggered configuration, where the first tip portion leads and the second tip portion follows. Accordingly, during a tissue collecting procedure, the first tip portion is configured to contact and engage the tissue to be sampled prior to the second tip portion. In some embodiments, the first and second tip portions are on opposing sides of the body. In some embodiments, the first and second tip portions are spaced apart in the range of 175 to 180 degrees along a circumference of the body.

The first tip portion is formed from a first set of distinct angular bevel grinds oblique to the longitudinal axis of the body and the second tip portion is formed from a second set of distinct angular bevel grinds oblique to the longitudinal axis of the body. The first set of angular bevel grinds includes first bevel grind on one side of the body and a second bevel grind on an opposing side of the body. The first and second bevel grinds converge with one another to define a first forward cutting edge of a penetrating tip of the first tip portion. In some embodiments, the first forward cutting edge is substantially perpendicular to the longitudinal axis of the body.

The first and second bevel grinds define first and second angles, respectively, relative to an outer surface of the body. In some embodiments, the first and second angles are in the range of 5 to 25 degrees. In some embodiments, the first and second angles are the same. The first set of angular bevel grinds further includes a back-cut bevel grind defining a substantially planar surface adjacent to the penetrating tip and defining a back-cut angle relative to an outer surface of the body and oblique to the outer surface of the body and the first and second bevel grinds. In some embodiments, the back-cut angle is 30 degrees.

The second set of angular bevel grinds includes a third bevel grind on one side of the body and a fourth bevel grind on an opposing side of the body. The third and fourth bevel grinds converge with one another to define a second forward cutting edge of a penetrating tip of the second tip portion. In some embodiments, the second forward cutting edge defines an oblique angle relative to the outer surface of the body, wherein the angle is in the range of 10 to 45 degrees. The third and fourth bevel grinds define third and fourth angles, respectively, relative to an outer surface of the body. In some embodiments, the third and fourth angles are in the range of 15 to 60 degrees. In some embodiments, the third and fourth angles are the same.

In some embodiments, the first set of bevel grinds includes a first bevel grind converging with a second bevel grind to form a penetrating tip of the first tip portion and the second set of bevel grinds includes a third bevel grind converging with a fourth bevel grind to form a penetrating tip of the second tip portion, wherein the first and third bevel grinds are one half of the body and intersect one another along a first intersection line and the second and fourth bevel grinds are on the other half of the body and intersect one another along a second intersection line. In some embodiments, the distal end includes at least four cutting edges formed between the first and second tip portions. A first cutting edge extends from the first intersection line to the penetrating tip of the first tip portion, a second cutting edge extends from the first intersection line to the penetrating tip of the second tip portion, a third cutting edge extends from the second intersection line to the penetrating tip of the first tip portion, and a fourth cutting edge extends from the second intersection line to the penetrating tip of the second tip portion. Each of the four cutting edges is configured to excise tissue upon contact therewith.

In some embodiments, the body may include a section having enhanced echogenicity or acoustic reflection. In some embodiments, the needle may further include a collet surrounding a portion of the body and having a diameter sufficient to prevent the body from entirely passing through a distal end of a sheath of a biopsy device.

In another aspect, the present disclosure includes a device for needle biopsy. The device includes an adjustable delivery handle system including a delivery handle, at least a portion of which includes an inner lumen configured to receive one of a plurality of exchangeable needle subassemblies. The adjustable delivery handle system further includes a sheath coupled to a distal end of the handle and having a lumen in fluid communication with the inner lumen of the delivery handle. The device further includes a needle subassembly removably disposed within the inner lumen of the delivery handle and lumen of the sheath, the needle subassembly including an exchangeable biopsy needle. The biopsy needle generally includes an elongate tubular body having a longitudinal axis and has lumen extending therethrough from a proximal open end to a distal open end of the body. The distal end includes first and second tip portions extending therefrom. The first tip portion generally extends further from the distal end than the second tip portion, resembling a staggered configuration, where the first tip portion leads and the second tip portion follows. Accordingly, during a tissue collecting procedure, the first tip portion is configured to contact and engage the tissue to be sampled prior to the second tip portion.

DETAILED DESCRIPTION

By way of overview, the present disclosure is generally directed to a biopsy needle configured for collecting tissue, fluid, and/or cell samples in conjunction with minimally-invasive procedures, such as endoscopic biopsy procedures. As described in greater detail herein, a biopsy needle consistent with the present disclosure may be used in Endoscopic Ultrasound (EUS) and Endobronchial Ultrasound (EBUS) procedures, particularly EUS Fine Needle Aspiration (FNA), EUS Fine Needle Biopsy (FNB), EUS Coring, and EBUS procedures for the purpose of harvesting tissue specimen from a targeted site. It should be noted, however, that the biopsy needle may be used in other minimally-invasive procedures, and is not limited to EUS and/or EBUS procedures.

In one aspect, a biopsy needle consistent with the present disclosure includes an elongate tubular body having a longitudinal axis and a lumen extending therethrough from a proximal open end to a distal open end of the body. The distal end includes at least a first tip portion and a second tip portion that radially oppose one another on either side of the needle body. The first tip portion is longer than the second tip portion, resulting in an increase in the surface area of a cutting edge extending between the first and second tip portions, particularly when compared to the cutting surface of a beveled leading distal end of a conventional biopsy needle (e.g., see the needle of FIGS. 1 and 2).

Because the first tip portion is longer than the second tip portion, the first tip portion is configured to initially pierce the tissue to be sampled with little or no resistance and further guide the sample tissue into the lumen of the biopsy needle. As the tissue is guided toward the lumen, the second tip portion captures and leads additional tissue towards the lumen. During this process the tissue is excised by the cutting edge, creating a contiguous core biopsy sample. By increasing the effective cutting surface area and having the staggered configuration of first and second tip portions, the biopsy needle of the present disclosure is able to guide tissue into the lumen in a controlled manner and maximize the amount of tissue harvested, particularly upon aspiration.

The distinct distal cutting end of a biopsy needle consistent with the present disclosure is configured to collect a full core of tissue sample while keeping the full core intact. Accordingly, a biopsy needle consistent with the present disclosure is configured to maximize tissue sampling yield and further ensure collection of a cohesive unit of sampled tissue so as to provide a more complete sample for testing, which may improve the accuracy and/or timing of diagnosis.

Figure 3:
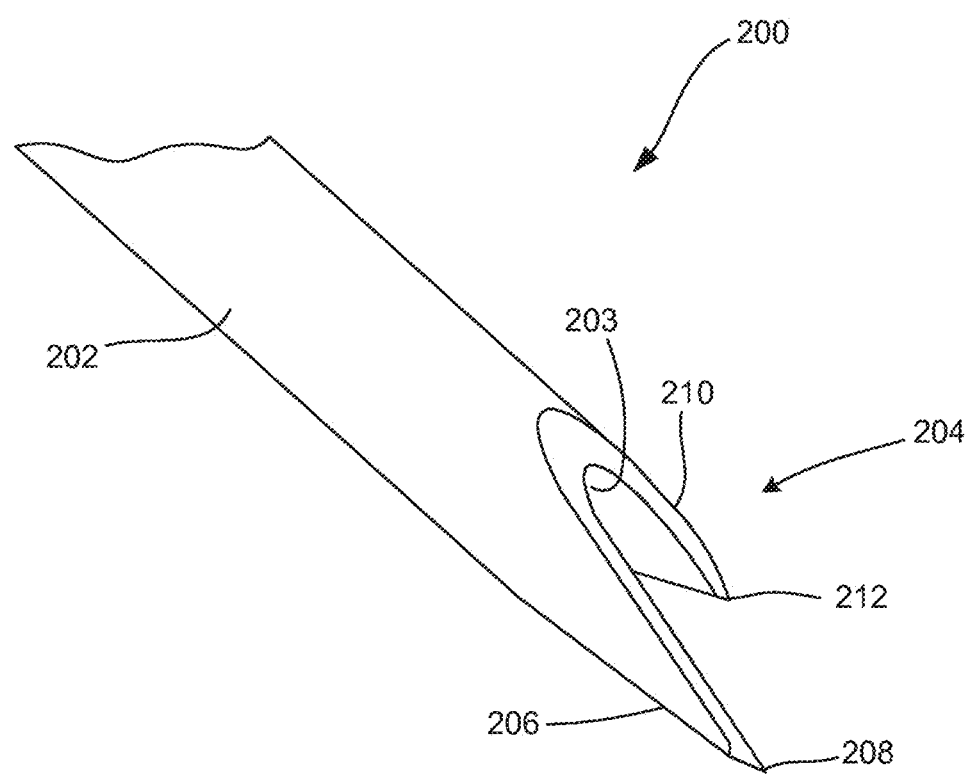
FIG. 3 is a perspective view of a portion of a biopsy needle consistent with the present disclosure.
Figure 4:
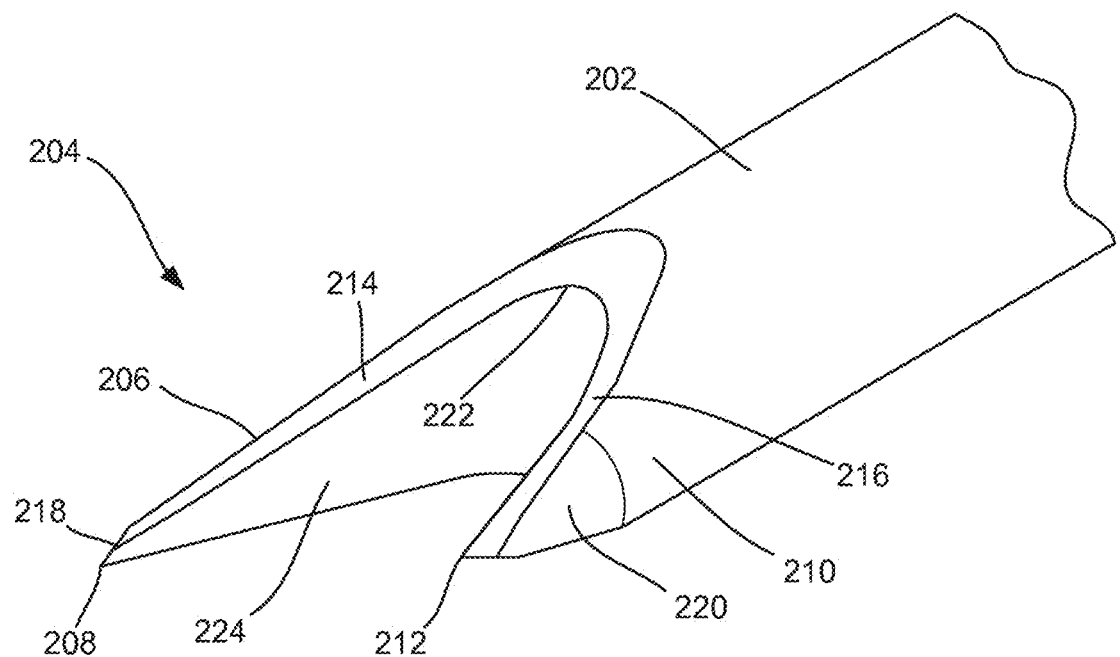
FIG. 4 is a perspective view of a portion of a biopsy needle consistent with the present disclosure.

FIGS. 3 and 4 show a distal portion a biopsy needle 200 consistent with the present disclosure. As shown, the needle 200 generally includes an elongate tubular body 202 having a lumen 203 extending through the body 202 from a proximal open end (not shown) to a distal open end 204. The distal end 204 is configured for collection and harvesting of a sample, including, but not limited to, tissue, fluid, and/or cell samples. In particular, the distal end 204 is beveled in a distinct configuration so as to enhance the ability of the needle 200 to penetrate and collect tissue during sample acquisition.

The distal end 204 includes a first tip portion 206 and a second tip portion 210 extending therefrom, wherein the first and second tip portions 206, 210 are formed on opposing sides of the needle body 202, such that the tip portions radially oppose one another. The first and second tip portions 206, 210 each include a point 208, 212, respectively. The points 208, 212 are configured to penetrate a tissue sample, with relatively little or no resistance during tissue sampling procedure and further configured to direct tissue towards the lumen 203 of the body 202.

The first tip portion 206 is generally formed from at least a first bevel grind 214 (shown on one side of the needle body 202) and the second tip portion 210 is formed from at least a second bevel grind 216, wherein the first and second bevel grinds 214, 216 are different from one another. The differing bevel grinds 214, 216 result in different lengths of the first and second tip portions 206, 210. For example, the first tip portion 206 has a length $L_1$ and the second tip portion 210 has a length $L_2$. The lengths $L_1$ and $L_2$ are each measured from an apex of an arcuate cutting edge shared between the first and second tip portions 206, 210 (shown in FIG. 6) and the corresponding points 208, 212. In the illustrated embodiment, $L_1$ is greater than $L_2$, such that the first tip portion 206 is essentially longer and extends further from apex than the second tip portion 210, such that the first and second tip portions 206, 210 are in a staggered configuration. As such, the first tip portion 206 is configured to contact and engage tissue to be sampled prior to contact and engagement of tissue by the second tip portion 210, which provides associated benefits, as will be described in greater detail herein. In some embodiments, at least one of the first and second tip portions 206, 210 includes a back-cut grind 218, 220 adjacent the respective point 208, 212. Among other benefits, the back-cut grind 218, 220 is configured to provide a smooth needle passage during needle insertion and withdrawal during a biopsy procedure, described in greater detail herein.

The distal end 204 further includes at least one curvilinear, or arcuate, cutting edge 222 extending between the first tip portion 206 and the second tip portion 210. The cutting edge 222 is generally formed by the first and second bevel grinds 214, 216 of the first and second tip portions 206, 210. During a tissue collection procedure, the cutting edge 222 is configured to excise tissue upon contact therewith and further allow the excised tissue sample to translate into the lumen 203 and contact the internal surface 224 of the lumen 203 for harvesting.

Figure 5:
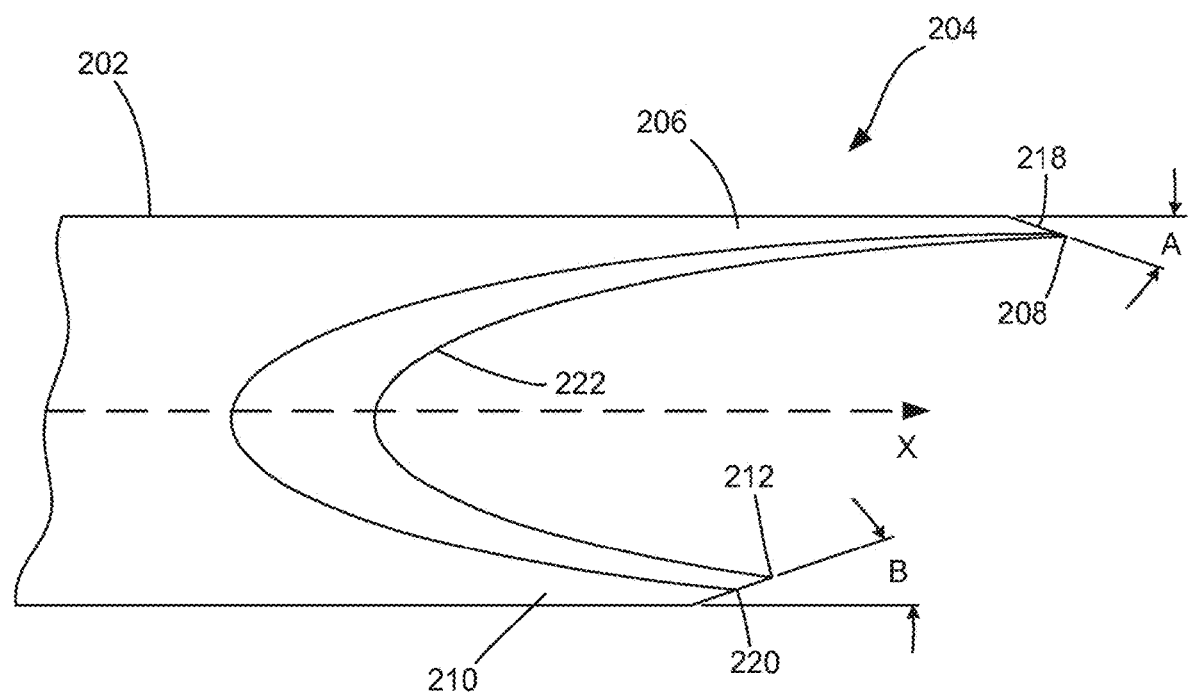
FIG. 5 is an enlarged side profile view of the distal end of the biopsy needle of FIGS. 3 and 4.

FIG. 5 is an enlarged side profile view of the distal end 204 of the biopsy needle 200. As shown, the cutting edge 222 generally extends entirely from the point 208 of the first tip portion 206 to the point 212 of the second tip portion 210. However, it should be noted that in other embodiments, the cutting edge 222 may only partially extend between distinct portions of the first and second tip portions 206, 210. In one embodiment, at least one of the first and second tip portions 206, 210 includes a back-cut grind. In another embodiment, i.e., as shown in the figures, both the first and second tip portions 206, 210 include a back-cut grind 218, 220, respectively. Each back-cut grind 218, 220 includes a back-cut angle oblique to an outer surface of the needle body 202. For example, back-cut grind 218 has a back-cut angle A and back-cut grind 220 has a back-cut angle B, wherein angles A and B are in the range of 15 degrees to 70 degrees, but more preferably in the range of 25 degrees to 45 degrees. In one embodiment, the back cut angles A and B are 30 degrees.

The inclusion of at least back-cut grind 218 on the first tip portion 206 may ensure the smooth passage of the needle down a sheath, or other enclosure of a delivery device, during needle movement and/or exchange. For example, the biopsy needle 200 of the present disclosure may be used in conjunction with a delivery device, such as an endoscopic device for delivering the needle 200 to the target site for tissue collection. The endoscopic device may generally include a sheath, or other enclosure, for provide the needle 200 with access to a target site for tissue collection. As such, during a needle exchange, for example, it is important that the needle 200 can be passed through an internal diameter of a sheath of the delivery device without catching on an internal wall of the sheath. As the needle advances, the heel of the back-cut grind 218 may come in contact with the internal diameter of the sheath and reduce the friction between the distal end 204 of the needle 200, particularly the point 208 of the first tip portion 206, and the sheath. In this way, the needle 200 can be smoothly tracked through the sheath to exit the end of the sheath. This feature also makes it easy to remove a needle and re-insert a new needle while the rest of a delivery device remains within a patient during a procedure.

Figure 6:
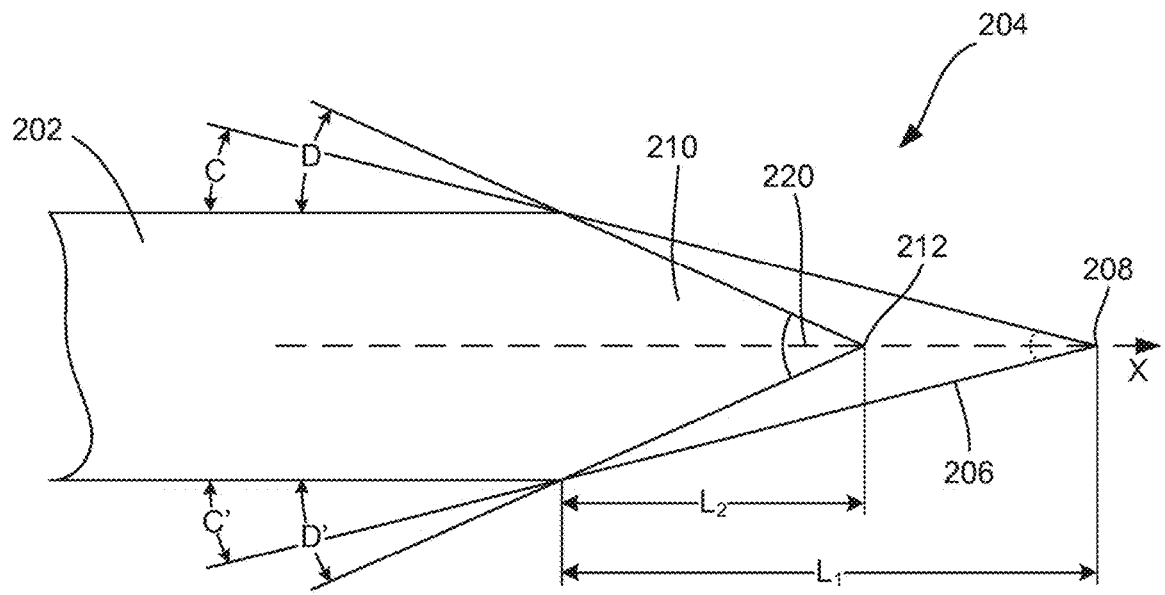
FIG. 6 is a bottom view of the distal end of the biopsy needle of FIGS. 3 and 4.

FIG. 6 is a bottom view of the distal end 204 of the biopsy needle 200 illustrating sets of bevel grinds that form the distal end 204. As shown, the first and second tip portions 206, 210 are formed from first and second sets of distinct angular bevel grinds that enhance tissue penetration and collection. For example, the first tip portion 206 is formed from a first set of distinct angular bevel grinds oblique to the longitudinal axis X of the needle body 202. The first set of angular bevel grinds comprises at least a first angle C on one side of the body 202 and a second angle C' on the opposing side of the body 202, wherein both angles C and C' are oblique to the longitudinal axis X of the body 202. In one embodiment, angles C and C' may be the same. In other embodiments, angles C and C' may be different. The first and second angles C and C' are in the range of 5 to 40 degrees. In some embodiments, the first and second angles C and C' are in the range of 5 to 20 degrees. In one embodiment, the first and second angles C and C' are 15 degrees.

Similarly, the second tip portion 210 is formed from a second set of distinct angular bevel grinds oblique to the longitudinal axis X of the needle body 202. The second set of angular bevel grinds comprises at least a third angle D on one side of the body 202 and a fourth angle D' on the opposing side of the body 202, wherein both angles D and D' are oblique to the longitudinal axis X of the body 202. In one embodiment, angles D and D' may be the same. In other embodiments, angles D and D' may be different. The third and fourth angles D and D' are in the range of 15 to 40 degrees. In some embodiments, the third and fourth angles D and D' are in the range of 20 to 30 degrees. In one embodiment, the third and fourth angles D and D' are 25 degrees. The first and second sets of angular bevel grinds described herein can be formed on the needle by any known processes, including, but not limited to, CNC needle grinding, laser cutting, and other needle tip forming techniques. Further, upon formation of the bevels, the distal end 204 undergoes treatment to remove all burrs and unwanted sharp edges as a result of the beveling process.

In the illustrated embodiment, the first and second sets of angular bevel grinds are different than one another. For example, in one embodiment, the first and second angles C and C' (forming the first tip portion 206) are approximately 15 degrees and the third and fourth angles D and D' (forming the second tip portion 210) are approximately 25 degrees. Accordingly, the first and second angles C and C' are less than the third and fourth angles D and D', resulting in the first and second tip portions 206, 210 having different associated lengths. For example, the first tip portion 206 has a length $L_1$ (measured from the point 208 to an apex of the arcuate cutting edge 222) and the second tip portion 210 has a length $L_2$ (measured from the point 212 to an apex of the arcuate cutting edge 222), wherein $L_1$ is greater than $L_2$. Accordingly, the first tip portion 206 is longer and extends further from the distal end 204 than the second tip portion 210, such that the first and second tip portions 206, 210 are in a staggered configuration and the first tip portion 206 leads during tissue collection. More specifically, the first tip portion 206 is configured to contact and engage tissue to be sampled prior to contact and engagement of tissue by the second tip portion 210. The lengths $L_1$ and $L_2$ of the first and second tip portions 206, 210 are in the range of 0.5 to 5 mm. In some embodiments, the length $L_1$ is in the range of 2 to 3 mm and the length $L_2$ is in the range of 0.5 to 1.5 mm. In one embodiment, the first tip portion 206 has a length $L_1$ of approximately 2.0618 mm and the second tip portion 210 has a length $L_2$ of approximately 1.3 mm. It should be noted that the first and second sets of angular bevel grinds may be manipulated so as to result in adjustment of lengths $L_1$ and $L_2$ of the first and second tip portions, respectively.

Figure 1:
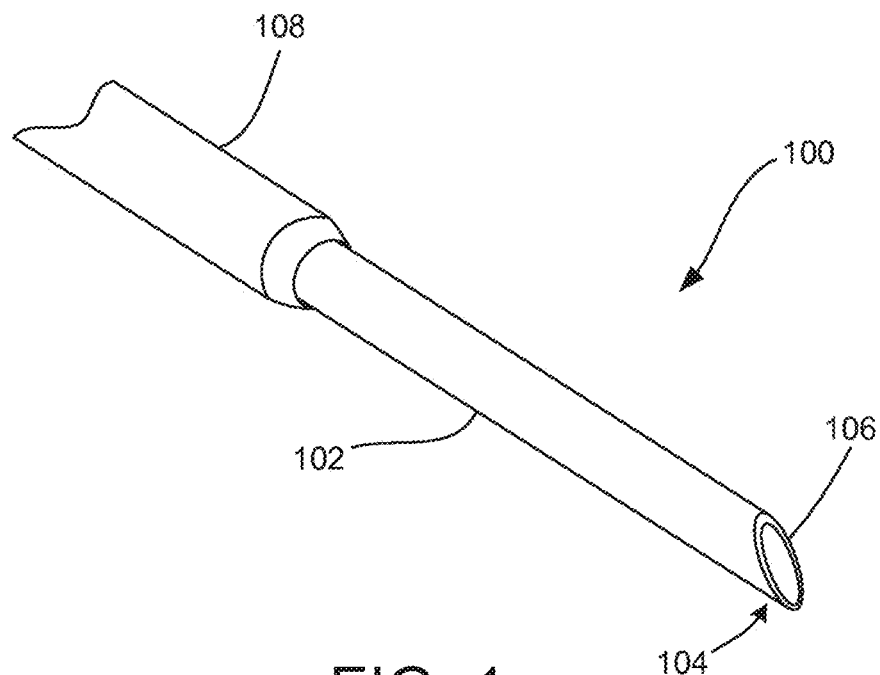
FIG. 1 is a perspective view of an embodiment of a biopsy needle known in the art.
Figure 2:
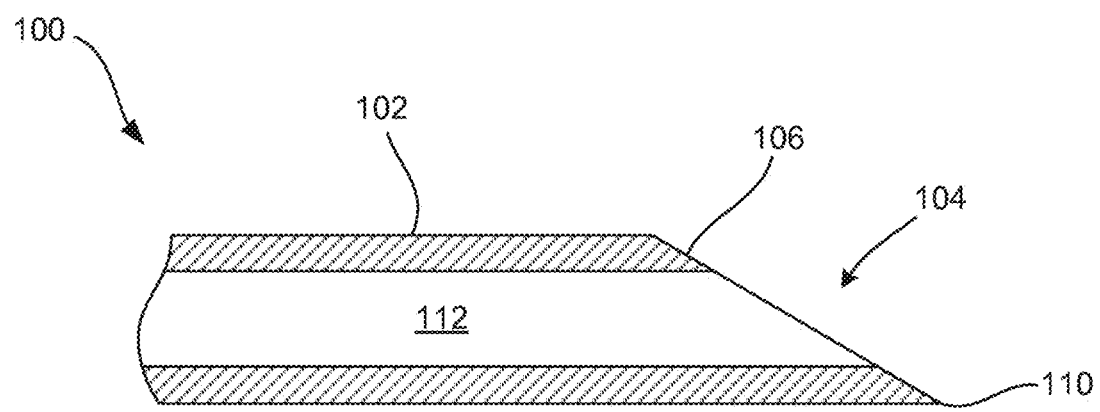
FIG. 2 is a cross-sectional view of the biopsy needle of FIG. 1.

The distinct configuration of the distal end 204 of the biopsy needle 200 is configured to maximize tissue sampling yield and further ensure collection of a cohesive unit of sampled tissue, thereby overcoming the drawbacks of current biopsy needles (such as needle 100 of FIGS. 1 and 2). For example, by providing a staggered configuration of the first and second tip portions 206, 210, the surface area of the effective cutting edge 222 is increased when compared to beveled leading distal ends of current biopsy needles (e.g., Menghini, Franseen, Quicke, etc.). Additionally, because the first tip portion 206 is longer than the second tip portion 210, the first tip portion 206 is configured to initially pierce the tissue to be sampled with little or no resistance and further guide the sample tissue into the lumen 203 of the biopsy needle 200. If the first and second tip portions 206, 210 were of equal length, it may prove more difficult to initially puncture of tissue sample, particularly a fibrous tissue. Furthermore, as the tissue is guided toward the lumen 203, the second tip portion 210 is further configured to capture and lead additional tissue towards the lumen 203 to be excised by the cutting edge 222 upon contact therewith. By increasing the effective cutting surface area and having the staggered configuration of first and second tip portions 206, 210, the biopsy needle 200 of the present disclosure is able to guide tissue into the lumen in a controlled manner and maximize the amount of tissue harvested, particularly upon aspiration.

Figure 7:
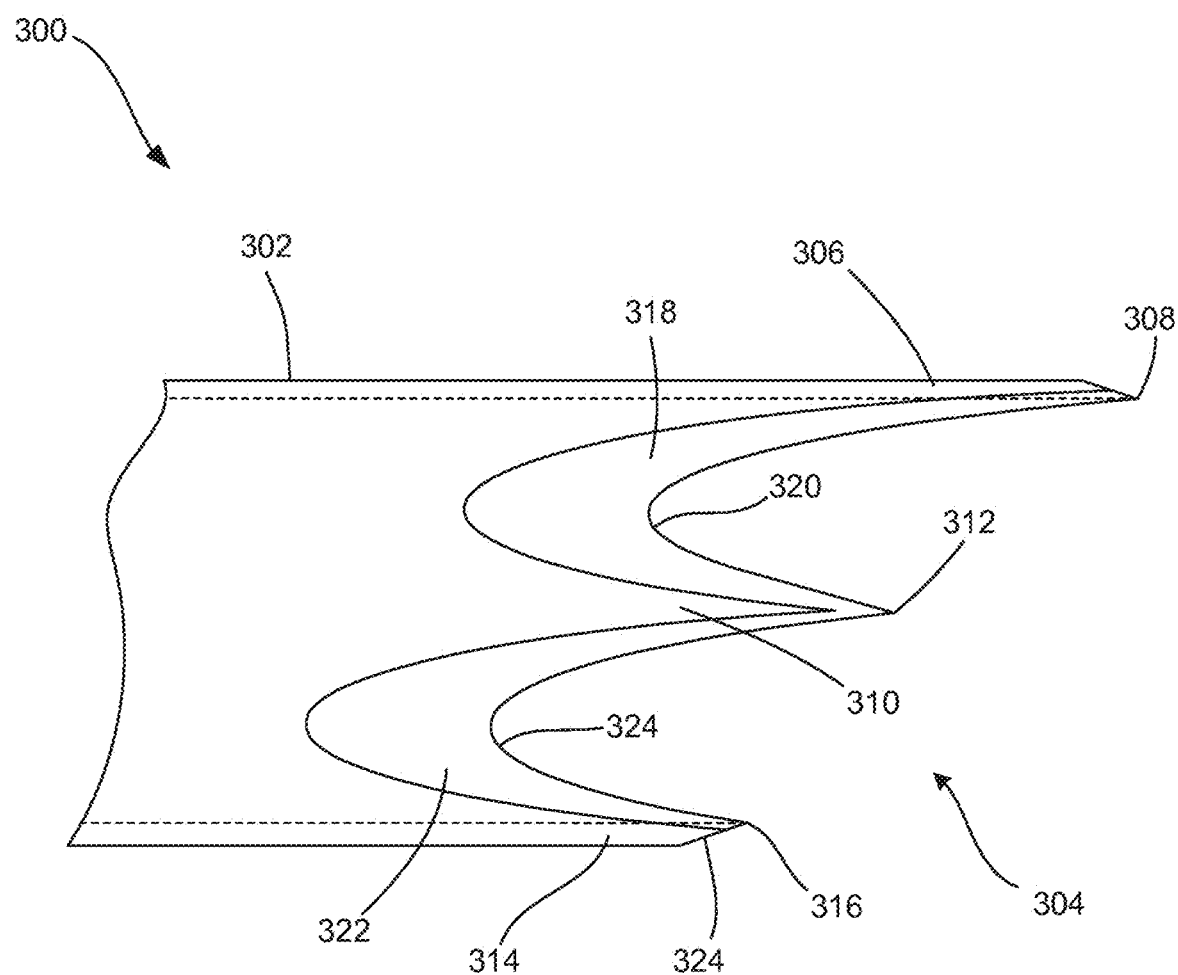
FIG. 7 is an enlarged side profile view of an alternative embodiment of a distal end of a biopsy needle consistent with the present disclosure.

It should be noted that a biopsy needle consistent with the present disclosure is not limited to the number of tip portions (e.g., two tip portions). For example, FIG. 7 is an enlarged side profile view of an alternative embodiment of a distal end 304 of a biopsy needle 300 having at least four tip portions extending from the distal end. As shown, the needle 300 may include first and second tip portions 306, 314 (similar to needle 200), and an additional third tip portion 310 and fourth (generally opposite the third 310) tip portion formed between the first and second tip portions 306, 314, wherein the first and second tip portions 306, 314 radially oppose one another on either side of the needle body 302 and the third and fourth tip portions radially oppose one another on either side of the needle body 302. As shown, the first tip portion 306 is longer than the third (and fourth) tip portion 310, which is longer than the second tip portion 314, such that distal end 304 maintains a staggered configuration. The inclusion of additional tip portions may further increase the surface area of cutting edges 320, 324 formed between the tip portions, which may be particularly beneficial when sampling certain types of tissue that may prove to be tough or resistant to cutting (e.g., fibrous tissue).

FIGS. 8-12 illustrate another embodiment of a biopsy needle 400 having a distal end 404 beveled in a distinct configuration so as to enhance the ability of the needle 400 to penetrate and collect tissue during sample acquisition. As shown, and described in greater detail herein, the distal end 404 includes at least five angular bevel grinds resulting in the formation of two opposing tip portions arranged in a staggered configuration, such that one of the tip portions is longer than the other, and multiple cutting edges are further defined between the opposing tip portions. As described in greater detail herein, this distinct distal cutting end is designed to overcome the drawbacks of current biopsy needles, which either provide an insufficient amount of a sample for analysis and/or damage a sample during the collection process.

Figure 8:
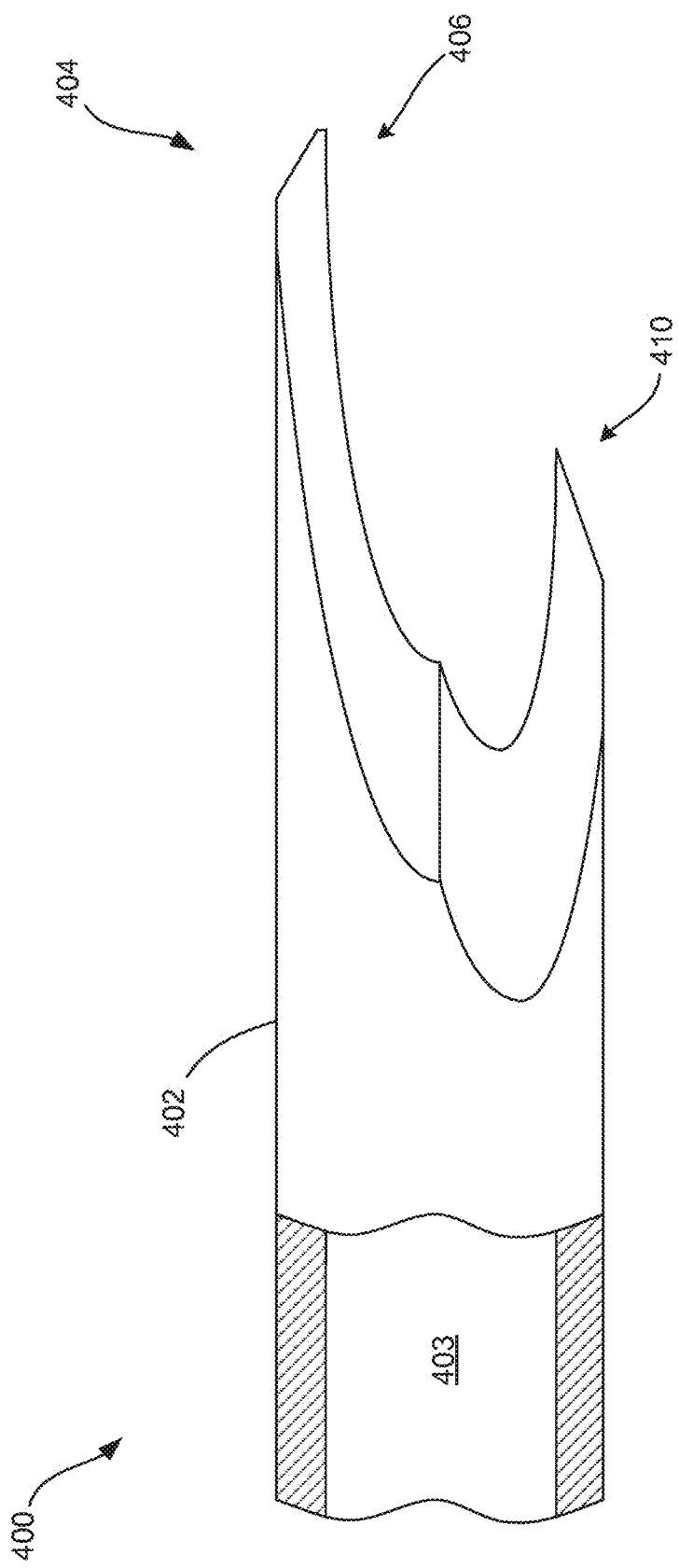
FIG. 8 is an enlarged side profile view, partly in section, of a distal end of another embodiment of a biopsy needle consistent with the present disclosure.
Figure 9:
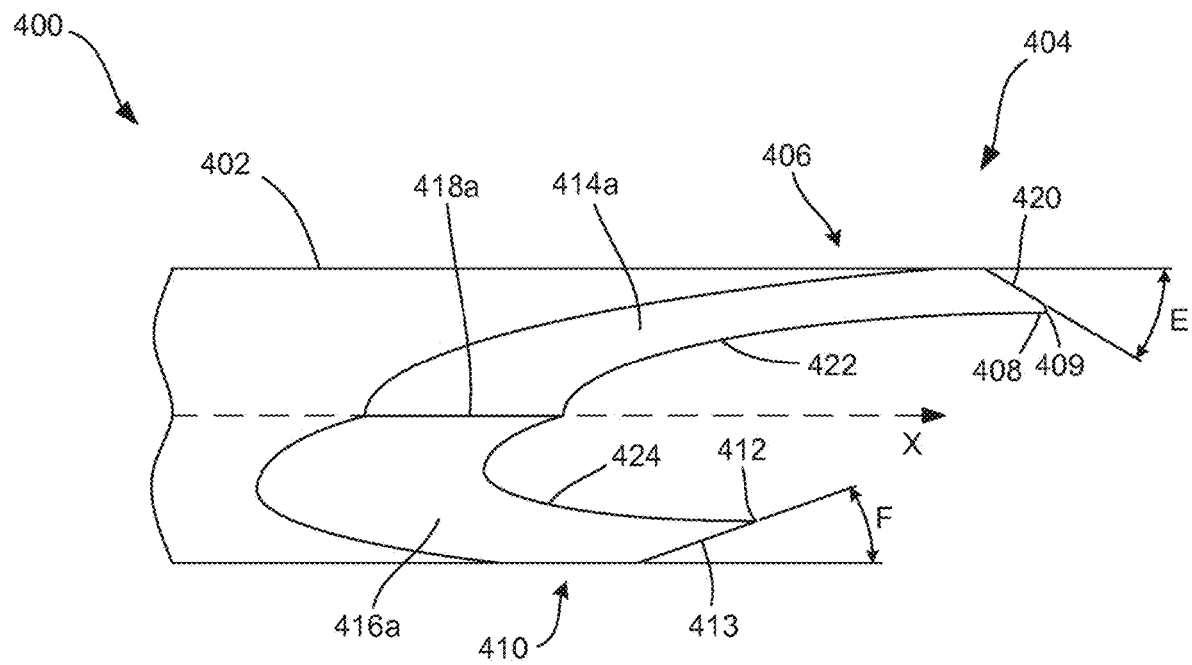
FIG. 9 is an enlarged side profile view of the distal end of the biopsy needle of FIG. 8 in greater detail.
Figure 10:
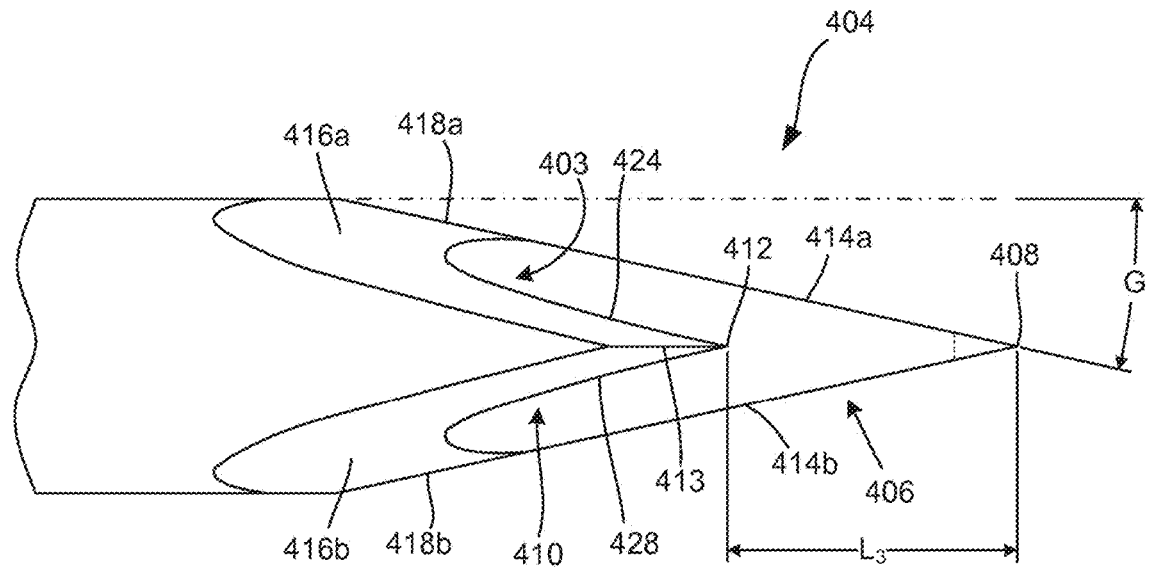
FIG. 10 is a bottom view of the distal end of the biopsy needle of FIG. 8.
Figure 11:
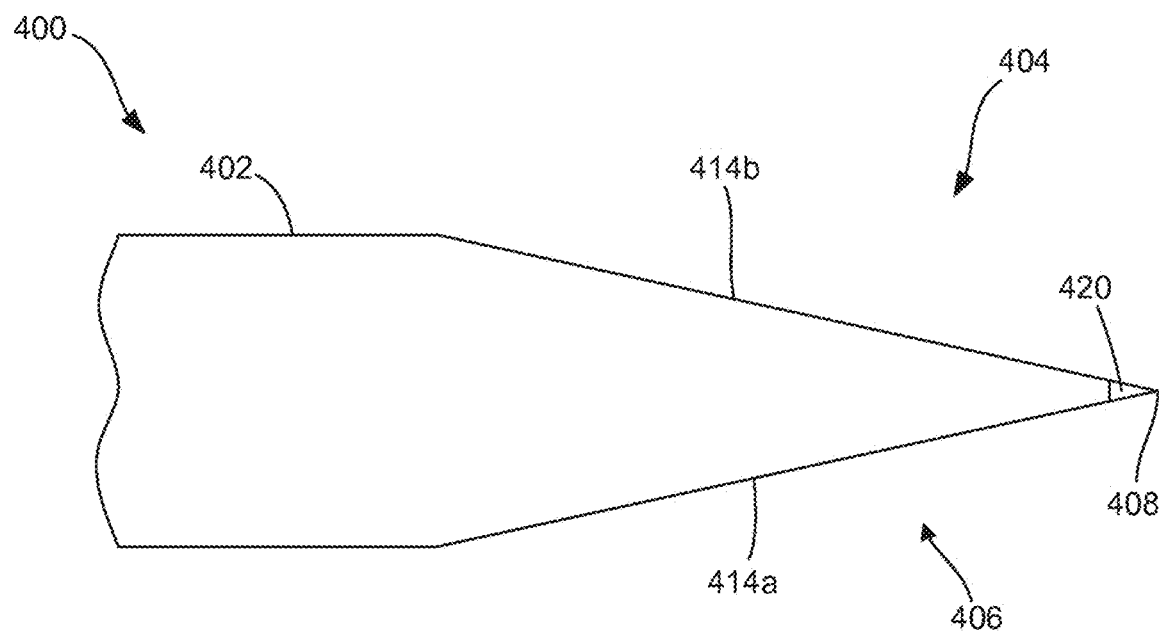
FIG. 11 is a top view of the distal end of the biopsy needle of FIG. 8.
Figure 12:
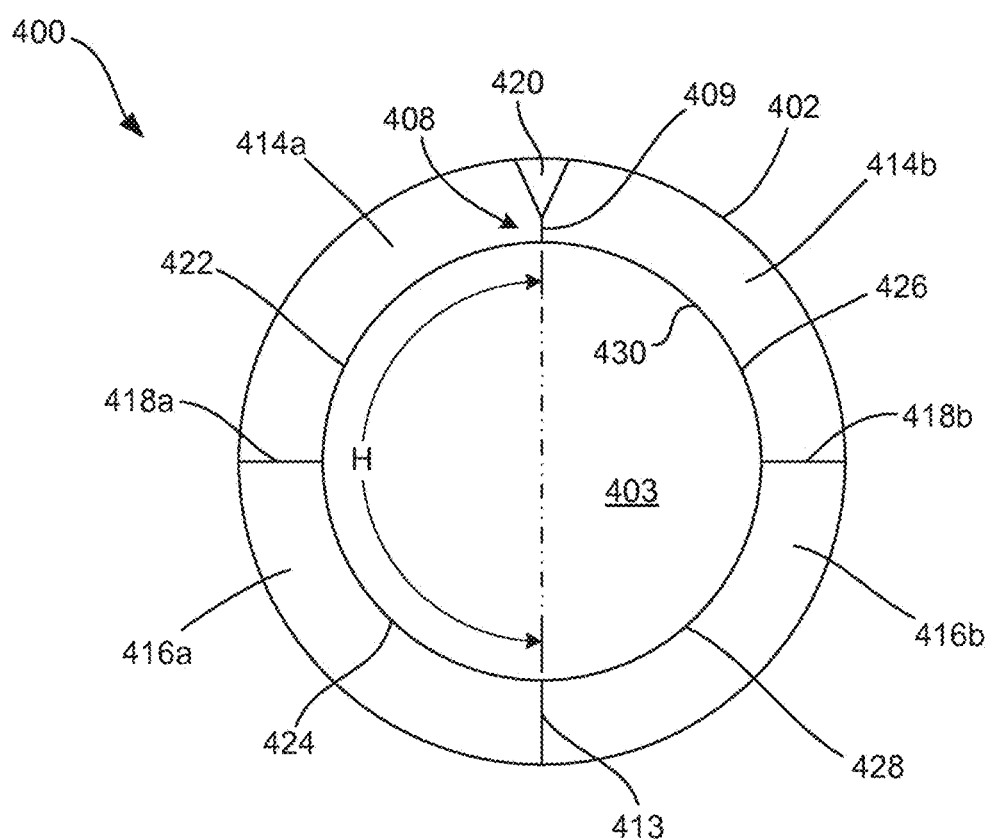
FIG. 12 is a front view of the distal end of the biopsy needle of FIG. 8.

FIG. 8 is an enlarged side profile view, partly in section, of the distal end 404 of the biopsy needle 400. FIG. 9 is an enlarged side profile view of the distal end 404 in greater detail and FIG. 10 is a bottom view of the distal end 404. FIGS. 11 and 12 are top and front views, respectively, of the distal end 404 of the biopsy needle 400. As shown, the needle 400 generally includes an elongate tubular body 402 having a lumen 403 extending through the needle body 402 from a proximal open end (not shown) to a distal open end 404. The distal end 404 is configured for collection and harvesting of a sample, including, but not limited to, tissue, fluid, and/or cell samples. In the illustrated embodiment, the distal end 404 includes a first tip portion 406 and a second tip portion 410 formed on opposing sides of the needle body 402, such that the tip portions 406, 410 generally oppose one another. The first and second tip portions 406, 410 each include a penetrating tip 408, 412, respectively, configured to penetrate a tissue sample, with relatively little or no resistance during tissue sampling procedure and further configured to direct tissue towards the lumen 403 of the body 402.

The first and second tip portions 406, 410 are formed from first and second sets of distinct angular bevel grinds configured to enhance tissue penetration and collection. For example, the first tip portion 406 is formed from a first set of distinct angular bevel grinds oblique to the longitudinal axis X of the needle body 402. As shown, the first tip portion 406 is formed from a first bevel grind 414a on one side of the needle body 402 and a second bevel grind 414b on an opposing side of the body, wherein the first and second bevel grinds 414a, 414b converge with one another to define a forward cutting edge 409 of the penetrating tip 408. In some embodiments, the forward cutting edge 409 may substantially perpendicular to the longitudinal axis X of the needle body 402. In other embodiments, the forward cutting edge 409 may be oblique to the longitudinal axis X.

As shown, the first and second bevel grinds 414a, 414b may be substantially similar and thus each defines a similar angle relative to the needle body 402. Accordingly, for ease of description, only one angle, as defined by the first bevel grind 414a, is shown and described. For example, the first bevel grind 414a defines an angle G relative to an outer surface of the needle body 402, wherein angle G is acute and in the range of 5 to 40 degrees. In some embodiments, angle G is in the range of 10 to 20 degrees. In one embodiment, angle G is 12 degrees. It should be noted that in some embodiments, the first and second bevel grinds 414a, 414b may be different (e.g., have different lengths, define different angles, etc.).

The first tip portion 406 may further include a back-cut bevel grind 420 forming a substantially planar surface adjacent to the penetrating tip 408. The back-cut bevel grind 420 generally defines a back-cut angle oblique to an outer surface of the needle body 202 and the first and second bevel grinds 414a, 414b. For example, back-cut bevel grind 420 generally defines a back-cut angle E in the range of 15 degrees to 70 degrees, but more preferably in the range of 25 degrees to 45 degrees. In one embodiment, the back cut angle E is 30 degrees. Similar to the back-cut bevel grinds of needle 200, the inclusion of the back-cut bevel grind 420 on the first tip portion 406 may ensure the smooth passage of the needle 400 down a sheath, or other enclosure of a delivery device, during needle movement and/or exchange. For example, the biopsy needle 400 of the present disclosure may be used in conjunction with a delivery device, such as an endoscopic device for delivering the needle 400 to the target site for tissue collection. The endoscopic device may generally include a sheath, or other enclosure, for provide the needle 400 with access to a target site for tissue collection. As such, during a needle exchange, for example, it is important that the needle 400 can be passed through an internal diameter of a sheath of the delivery device without catching on an internal wall of the sheath. As the needle advances, the heel of the back-cut bevel grind 420 may come in contact with the internal diameter of the sheath and reduce the friction between the distal end 404 of the needle 400, particularly the penetrating tip 408 of the first tip portion 406, and the sheath. In this way, the needle 400 can be smoothly tracked through the sheath to exit the end of the sheath. This feature also makes it easy to remove a needle and re-insert a new needle while the rest of a delivery device remains within a patient during a procedure.

The second tip portion 410 is formed from a second set of distinct angular bevel grinds oblique to the longitudinal axis X of the needle body 402. As shown, the second tip portion 410 is formed from a third bevel grind 416a on one side of the needle body 402 and a fourth bevel grind 416b on an opposing side of the body, wherein the third and fourth bevel grinds 416a, 416b converge with one another to define a forward cutting edge 413 of the penetrating tip 412. In some embodiments, the forward cutting edge 413 may substantially perpendicular to the longitudinal axis X of the needle body 402. In other embodiments, the forward cutting edge 413 may be oblique to the longitudinal axis X. For example, in the illustrated embodiment, the forward cutting edge 413 defines an oblique angle F relative to the outer surface of the needle body 402, wherein angle F is acute and in the range of 5 to 80 degrees. In some embodiments, angle F is in the range of 10 to 60 degrees. In one embodiment, angle F is 20 degrees.

As shown in FIG. 9, the first bevel grind 414a and third bevel grind 416a are formed on one half of the needle body 402, such that the first and third bevel grinds 414a, 416a intersect one another along a first intersection line 418a. In some embodiments, the first intersection line 418a defines an oblique angle relative to the longitudinal axis X of the needle body 402. Similarly, the second bevel grind 414b and fourth bevel grind 416b are formed on the other half of the needle body 402, such that the second and fourth bevel grinds 414b, 416b intersect one another along a second intersection line 418b opposite the first intersection line 418a. In some embodiments, the second intersection line 418b defines an oblique angle relative to the longitudinal axis X of the needle body 402. As shown, the third and fourth bevel grinds 416a, 416b may be substantially similar and thus each defines a similar angle relative to the outer surface of the needle body 402. In some embodiments, each of the third or fourth bevel grinds 416a, 416b may define an acute angle in the range of 15 to 60 degrees.

The distal end 404 of the needle 400 further includes multiple cutting edges as formed by the multiple bevel grinds. As shown in FIGS. 8-12, a first cutting edge 422 is defined along one side of the first tip portion 406, extending from the penetrating tip 408 to the first intersection line 418a in a generally arcuate configuration. The first cutting edge 422 is generally formed by the first bevel grind 414a. A second cutting edge 424 is defined along one side of the second tip portion 410, extending from the penetrating tip 412 to the first intersection line 418a in a generally arcuate configuration. The second cutting edge 424 is generally formed by the second bevel grind 414a. As shown in FIG. 12, a third cutting edge 426 is defined along the other side of the first tip portion 406, extending from the penetrating tip 408 to the second intersection line 418b in a generally arcuate configuration and a fourth cutting edge 428 is defined along the other side of the second tip portion 410, extending from the penetrating tip 412 to the second intersection line 418b in a generally arcuate configuration. During a tissue collection procedure, each of the cutting edges (e.g., forward cutting edges 409 and 413, and first, second, third, and fourth cutting edges 422-428) is configured to excise tissue upon contact therewith and further allow the excised tissue sample to translate into the lumen 403 and contact the internal surface 430 of the lumen 403 for harvesting.

As shown in FIGS. 8-10, the first and second tip portions 406, 410 are of different lengths, wherein the first tip portion 406 extends further from the needle body 402 than the second tip portion 410, such that the first and second tip portions 406, 410 are in a staggered configuration. As such, during movement of the needle body 402 in a direction towards a surface of the tissue to be sampled, the first tip portion 406 is configured to contact and engage the tissue prior to contact and engagement of tissue by the second tip portion 410, which provides associated benefits, as will be described in greater detail herein.

As shown in FIG. 10, for example, the penetrating tip 408 of the first tip portion 406 extends further from the needle body 402 than the penetrating tip 412 of the second tip portion 410, such there is a difference in length $L_3$ between the penetrating tips 408, 412. For example, in one embodiment, the difference in length $L_3$ is at least 0.021 mm. In another embodiment, the difference in length $L_3$ is at least 0.028 mm. In another embodiment, the difference in length $L_3$ is at least 0.051 mm.

The first and second tip portions 406, 410 are generally formed on opposing sides of the needle body 402, as shown in FIGS. 8-12. For example, as shown in FIG. 12, when viewing the needle 400 from a front distal end view, the penetrating tips 408, 412 of the first and second tip portions 406, 410, respectively, radially oppose one another. An angle H may be defined between the forward cutting edges 409, 413 of the penetrating tips 408, 412 when viewed along the longitudinal axis X (view depicted in FIG. 12). In some embodiments, angle H may be in the range of 100 to 180 degrees. In some embodiments, angle H may be in the range of 125 to 180 degrees. In some embodiments, angle H may be in the range of 150 to 180 degrees. In some embodiments, angle H may be in the range of 175 to 180 degrees. In one embodiment, angle H may be 180 degrees. Accordingly, in one embodiment, the first and second tip portions 406, 410 may be spaced apart approximately 180 degrees, plus or minus 5 degrees, along a circumference of the needle body 402.

The distinct distal end 404 configuration results in numerous advantages over the conventional needle tip. For example, by forming the first tip portion 406 longer than the second tip portion 410, an increase in the surface area of cutting edges 422-428 extending between the tip portions 406, 410 is achieved. By increasing the effective cutting surface areas, the distal end 404 is able to maximize the amount of tissue to be harvested. The staggered configuration further ensures collection of a cohesive unit of sampled tissue. One of the drawbacks of current needle tip designs is that, as tissue is pierced and excised during tissue collection, the excised tissue may curl away from needle tip as it is advanced into the target tissue, resulting in a lost or incomplete sample. The staggered design is configured to overcome such a drawback. In particular, due to the staggered configuration, the leading first tip portion 406 is configured to initially pierce the tissue to be sampled prior to the following second tip portion 410. Upon advancing the needle 400 further into the tissue, the first tip portion 406 is configured to direct a sample of tissue in a direction towards the lumen 403 of the needle 400. As the needle 400 is forced further into the target tissue, the second tip portion 410, which is set back from first tip portion 406, is configured to catch and grab additional tissue that may have otherwise deflected off of the first tip portion 406 and may have missed the lumen 403 entirely, as is the case with some current needle tip designs. In this manner, a full core sample may be achieved.

The different embodiments of the biopsy needle of the present disclosure may be used in conjunction with minimally-invasive procedures, such as endoscopic procedures. For example, a biopsy needle consistent with the present disclosure may be compatible with an endoscopic biopsy device, such as needle biopsy delivery device configured for endoscopic ultrasound or endoscopic bronchial ultrasound procedures. For example, the biopsy needle may be compatible for use with exemplary endoscopic deliver systems and methods discussed in Needle Biopsy Device with Exchangeable Needle and Integrated Needle Protection, U.S. Pub. 2012/0116248, Rapid Exchange FNA Biopsy Device with Diagnostic and Therapeutic Capabilities, U.S. Pub. 2011/0190662, Device for Needle Biopsy with Integrated Needle Protection, U.S. Pub. 2010/0121218, and Needle Biopsy Device, U.S. Pub. 2010/0081965, the contents of each of which are hereby incorporated by reference in their entirety.

Figure 13:
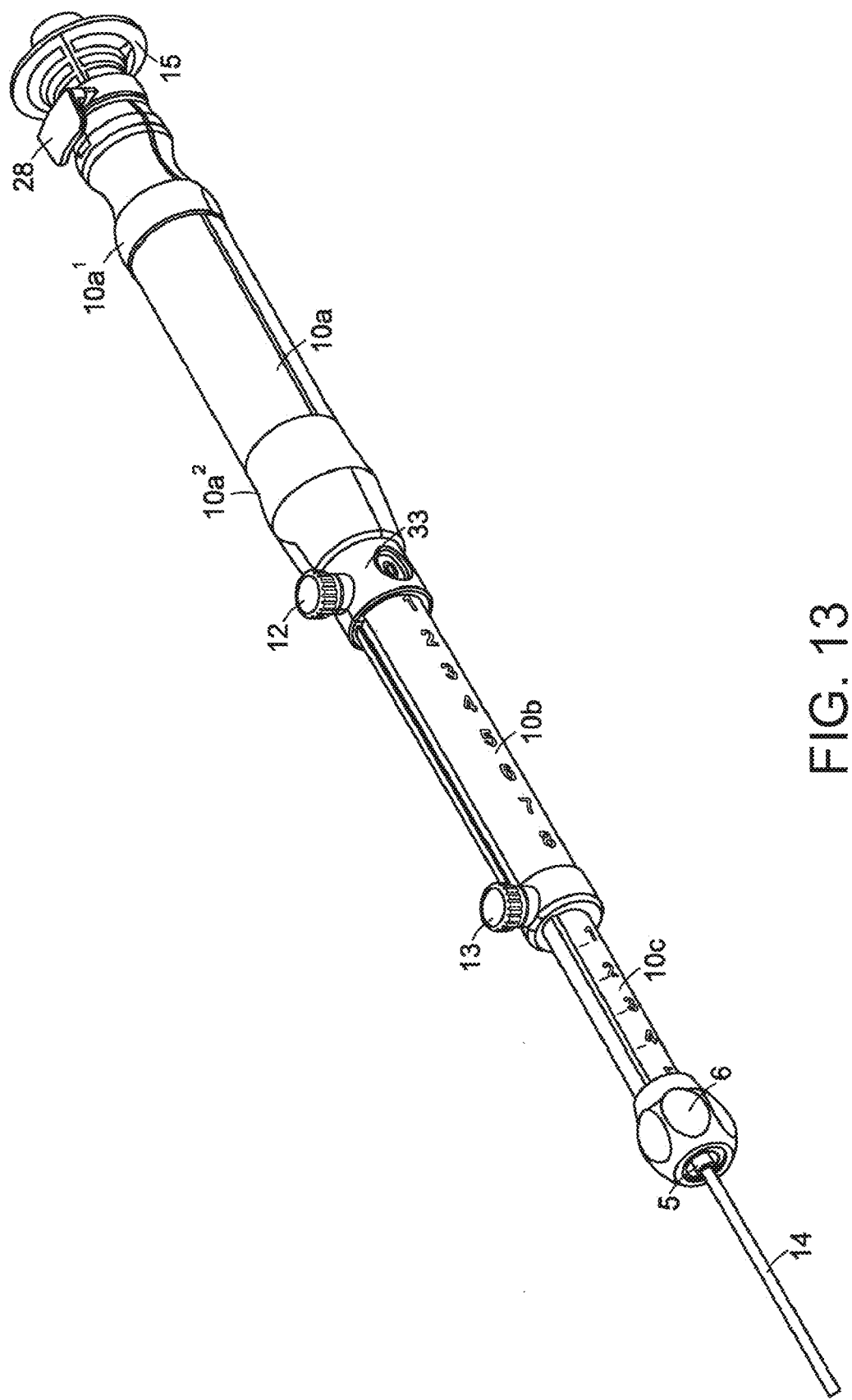
FIG. 13 is a perspective view of a biopsy device including an adjustable delivery handle and sheath for receipt of and use with an exchangeable biopsy needle consistent with the present disclosure.

An exemplary embodiment of an endoscopic delivery device assembly for use with a biopsy needle of the present disclosure is illustrated in FIG. 13. The device and specific delivery methods are discussed in more detail in Needle Biopsy Device with Exchangeable Needle and Integrated Needle Protection, U.S. Pub. 2012/0116248, the contents of which are hereby incorporated by reference in their entirety. The device design consists of a handle mechanism (delivery system handle 10) and removable needle sub-assembly 15. The delivery system handle 10 includes a proximal handle member 10a, a middle handle member 10b, and a distal handle member 10c. The proximal, middle and distal handle members each include an inner lumen and are coupled together to define a longitudinal axis such that the inner lumens are in constant communication and extends throughout the length of the coupled handle members. Proximal handle member 10a is slideably disposed over at least a portion of the middle handle member 10b, and middle handle member 10b is slideably disposed over at least a portion of distal handle member 10c. The proximal handle member 10a includes proximal handle grip 10a1 a distal handle grip 10a2. The delivery system handle 10 further includes an inner handle member 10d disposed within the inner lumen of the middle handle member 10b.

The delivery system handle 10 also incorporates a sheath 14 component coupled to the distal end of the distal handle member 10c. This component provides a conduit between the delivery system handle 10 and the target sampling site during the exchange of needles, such as the biopsy needle previously described herein. The device design is modular in that the needle sub-assembly 15 can be detached from the proximal handle member 10a of the device for each individual "pass" or aspirated sample taken by the endoscopist at the site of the lesion or abnormality.

The delivery system handle 10 incorporates two length adjustment features actuated via adjustment of two thumb-screw locking mechanisms. A threaded proximal thumb-screw 12 and locking ring 33 are moveably disposed around the middle handle member 10b, the proximal thumbscrew 12 is loosened to loosen locking ring 33, locking ring 33 is moved distally along the middle handle member 10b and tightened in the desired position along middle handle member 10b via proximal thumbscrew 12 to allow the user to establish a set depth of needle penetration beyond the end of the sheath 14. A threaded distal thumbscrew 13 is transversely disposed at the distal portion of the middle handle member 10b, the distal thumbscrew 13 is loosened to move the middle handle member 10b distally and/or proximally and tightened to allow the user to establish a set depth of sheath 14 extension beyond the end of the endoscope accessory channel.

The needle sub-assembly 15 consists of at least a biopsy needle consistent with the present disclosure (e.g., needle 200). The body 202 of needle 200 can range in length from 200 mm up to 2500 mm. In some embodiments, the needle body 202 can range in length between 500 mm to 2000 mm. In some embodiments, the needle body 202 can range in length between 800 mm to 1800 mm. In some embodiments, the needle body 202 can range in length between 1640 mm to 1680 mm. The needle sub-assembly 15 further includes needle hub 17, needle luer 18, needle collet 226, needle protector sub-assembly 9, stylet hub 20, and stylet shaft 22.

As generally understood, the needle 200 itself can be manufactured from a variety of metallic based materials, including, but not limited to, nitinol, cobalt chrome, stainless steel, a metal alloy, combinations thereof, or Polymeric Based materials including, but not limited to poly-ether-ether ketone, polyamide, poyethersulfone, polyurethane, ether block amide copolymers, polyacetal, polytetrafluoro-ethylene and/or derivatives thereof. It should be noted that the biopsy needle is not limited to any particular gauge (e.g., outer diameter). For example, depending on the type of sample to be collected, as well as the target site from which the sample is to be collected, the biopsy needle may range from 10-gauge to 30-gauge, and more specifically 15-gauge to 28-gauge, i.e., gauge 12, 14, 15, 16, 17, 18, 19, 20, 21, 22, 23, 24, or 25 needles.

Figure 14:
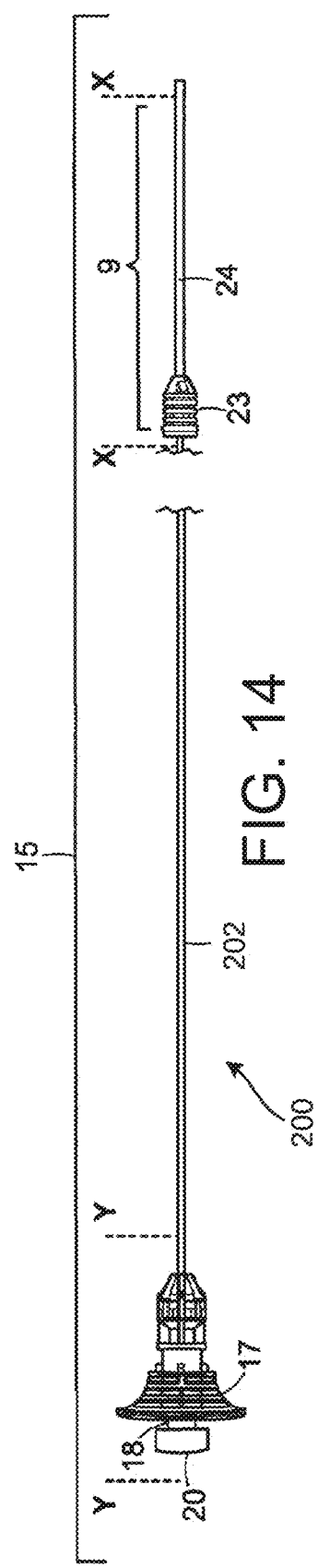
FIG. 14 is a drawing of the needle sub-assembly of the device of FIG. 13.

FIG. 14 is a drawing of the needle sub-assembly 15 of the device of FIG. 13. The needle sub-assembly 15 is inserted into and removed from the lumen of the delivery system handle 10 in acquiring tissue samples. The needle sub-assembly 15 consists of stylet hub 20 and stylet shaft 22 components which are securely locked on the needle luer 18 of the needle 200 via conventional internal luer threads, as generally understood by one skilled in the art. The stylet hub 20 may be attached to the stylet shaft 22 via any known processing techniques, including, but not limited to, adhesive bonding or insert injection molding. The female luer of the needle 200 incorporates a mating luer thread detail, onto which the stylet hub 20 may be tightened. The needle luer 18 element of the present disclosure may be attached to the proximal end of the needle shaft via a number of processing techniques such as adhesive bonding or insert injection molding.

The removable needle sub-assembly 15 also incorporates a needle collet 226. The function of this needle collet 226 is to provide a means to center the needle body 202 in the sheath 14 of the delivery system during needle exchange and provide a mechanism for securing and locking the needle protector sub-assembly to the distal end 204 needle 200 once the needle 200 has been unlocked and withdrawn from the delivery system handle. The needle collet 226 of the present disclosure may be attached to a portion of the needle body 202 near the distal end 204 of the needle 200 by way of any known processing techniques, including, but not limited to, adhesive bonding, laser welding, resistance welding, insert injection molding, and combinations thereof. The needle collet 226 may be fabricated from metals materials such as stainless steel, nickel titanium or alloys thereof or polymer materials such as, but not limited to, Polyacetal, polyamide, poly-ether-block-amide, polystyrene, Acrylonitrile butadiene styrene or derivatives thereof.

Figure 15:
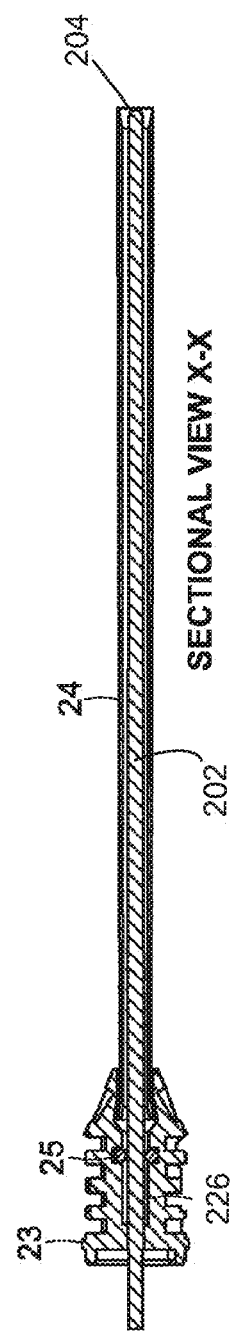
FIG. 15 is a cross sectional drawing of the needle protector embodiment of the needle sub-assembly of FIG. 14.

FIG. 15 illustrates the needle protector sub-assembly 9 design embodiment of the present disclosure in the locked position at the distal end 204 of the needle 200. The needle protector sub-assembly 9 consists of two needle protector (NP) hub halves (collectively 23), which are adhesively bonded to each other, on the proximal end of the needle protector (NP) sheath 24. Alternatively, the NP hub halves 23 may be snap fit together or may be insert injection molded over the NP sheath 24 to provide a secure bond/attachment between these components in the assembly. The needle protector sub-assembly 9 also incorporates a needle protector (NP) hub O-Ring 25. The O-Ring component resides in a recessed cut-out in the center of the assembled NP hub halves 23. The NP hub O-Ring 25, in conjunction with the needle collet 226, which is securely attached to a portion of the needle body 202 near the distal end 204 of the needle 200, provides a mechanism for locking the NP sub-assembly 9 onto the end of the needle 200. In this way, the distal end 204, including the first and second tip portions 206, 210 previously described herein, is protected, covered and shielded once the needle has been removed from the delivery system handle. For example, upon acquiring a sample from a target site, the needle 200 may be removed so as to gain access to the sampled material for testing and diagnostic procedures. The needle 200 may be continually withdrawn from the delivery system handle 10, such that the needle collet 226 contacts the NP hub O-ring 25 and further pulls the NP sub-assembly 9 from engagement with needle hub 17, such that the needle 200 is completely removed from the delivery system handle 10 and the NP sheath 24 encases the distal end 204 of the needle 200 to prevent inadvertent "needle sticking". Further, an operator may then pull back the NP sub-assembly 9 from the distal end 204 of the needle 200 so as to collect the sampled material stored within the lumen of the needle 200. Accordingly, the NP sub-assembly 9 is configured to translate along a length of the needle 200 so as to allow access to the distal end 204 of the needle 200 post acquisition and when the needle 200 is entirely removed from the delivery system handle 10.

Figure 16:
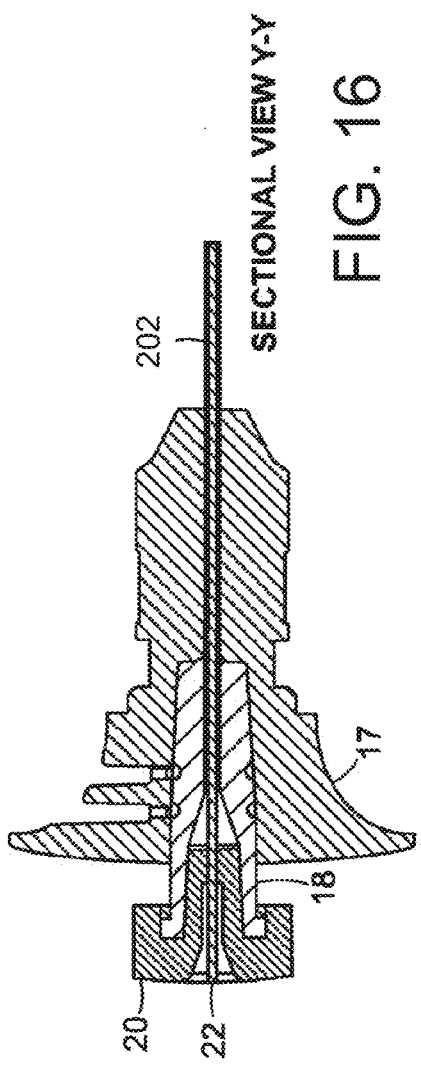
FIG. 16 is a cross sectional drawing of the needle hub at the proximal end of the biopsy needle sub-assembly of FIG. 14.

Referring the FIG. 16, the needle hub 17 embodiment of the needle sub-assembly is generally illustrated. The needle hub 17 provides a mechanism configured to lock the removable needle sub-assembly 15 into the delivery system handle 10 by means of the hub housing 27 and thumb latch 28 components and provide a means to lock the needle protector sub-assembly 9 embodiment shown in FIG. 15, into the delivery system handle 10. As shown in FIG. 16, the needle hub 17 is securely attached to the needle luer 18 and needle body 202. The needle hub 17 of the present disclosure may be attached to the distal end of the needle luer 18 via a number of processing techniques such as adhesive bonding or insert injection molding.

In some instances, it may be preferable to switch needles during a procedure, while still maintaining access to the target site. The delivery system of FIG. 13 is configured to allow rapid needle exchanges without requiring the delivery system to be removed from the scope, as described in greater detail in U.S. Pub. 2012/0116248, the contents of which are hereby incorporated by reference in their entirety. Accordingly, the sheath 14 may remain at a target site for an indefinite period of time while allowing the exchange of multiple needles. The rapid needle exchange capabilities provided by the delivery system of the present disclosure may further decrease the amount of time required for a biopsy procedure, which may cut down the amount of anesthesia required during a particular procedure, improving patient safety. Additionally, a new biopsy device is not required for each needle, as may be the case with current biopsy devices and techniques. Accordingly, the delivery system and exchangeable needles of the present disclosure can cut down on costs and by preventing unnecessary waste.

Figure 17:
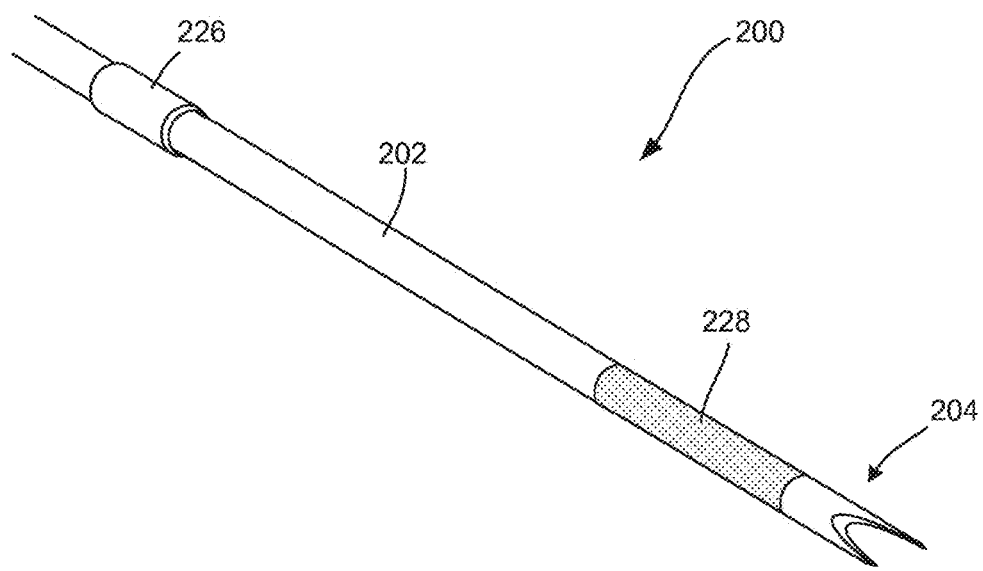
FIG. 17 is a perspective view of a biopsy needle consistent with the present disclosure.

FIG. 17 is a perspective view of a portion of the biopsy needle 200 near the distal end 204. As shown, the needle 200 further includes needle collet 226 coupled to a portion of the needle body 202. The length of the needle collet 226 may be in the range of 2 mm to 10 mm, but more preferably in the range of 3.5 mm to 5 mm. It is preferable that the outer diameter of the needle collet 226 be in the range of 0.030 inches to 0.080 inches, but more preferably in the range of 0.040 inches to 0.070 inches, depending on the gauge of the needle 200. The needle collet 226 may be chamfered at the proximal and distal ends thereof. In some embodiments, it may be preferable that the chamfer angle of the needle collet 226 be in the range of 15 degrees to 80 degrees, oblique to a longitudinal axis of the needle 200, but more preferably in the range of 30 degrees to 60 degrees. The chamfer on both ends of the needle collet 226 may provide smooth locking and unlocking with the needle protector sub-assembly 9 during needle exchanges.

The needle collet 226 is located at a set point distance from the distal end 204 of the needle 200. The distance from the distal end 204 of the needle to the proximal collet position on the needle 200 may be within the range of 6 cm to 12 cm, but is more preferably in the range of 7 cm to 9 cm, and more preferably is located 8 cm from the end of the needle 200. This ensures that when the needle is extended to a maximum extension distance relative to the distal tapered end 14a of the sheath (i.e. 8 cm), the needle collet 226 does not exit the end of sheath 14, as shown in FIGS. 18A and 18B.

In the illustrated embodiment, a region 228 of the needle body 202 adjacent the distal end 204 may incorporate an embodiment to enhance the echogenic signature of the needle 200. For example, this echogenically enhanced region 228 can be fabricated by, but not limited to, roughening the end of the needle over a pre-defined length adjacent to at least the first and second tip portions of the distal end 204. The length of the echogenically enhanced region 228 may be in the range of 2 mm to 20 mm, but is more preferably in the range of 10 mm to 15 mm. The echogenic enhanced region 228 may be imparted to the needle body 202 via a micro-blasting process which roughens the surface of the needle over a specific length, improving the visibility of the needle under endoscopic ultrasound. In other embodiments, the echogenically enhanced region 228 of the needle 200 may be achieved through the removal of material from the surface of the needle to provide greater reflectivity and strengthened reflected signal. It is contemplated that the removal of material does not, however, reduce the performance of the needle from a pushability perspective or deter its ability to acquire a desired sample.

It should be noted that other embodiments of a biopsy needle described herein, including needles 300 and 400, may also include the needle collet 226 and/or one or more portions having echogenically enhanced regions 228, as described with reference to needle 200.

Figure 18A:
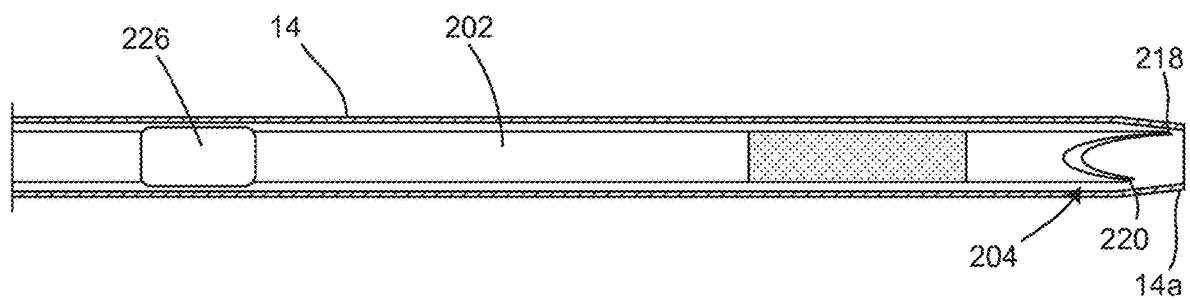
FIG. 18A is a side view, partly in section, of storage of the biopsy needle of FIG. 17 within the sheath of FIG. 13.
Figure 18B:
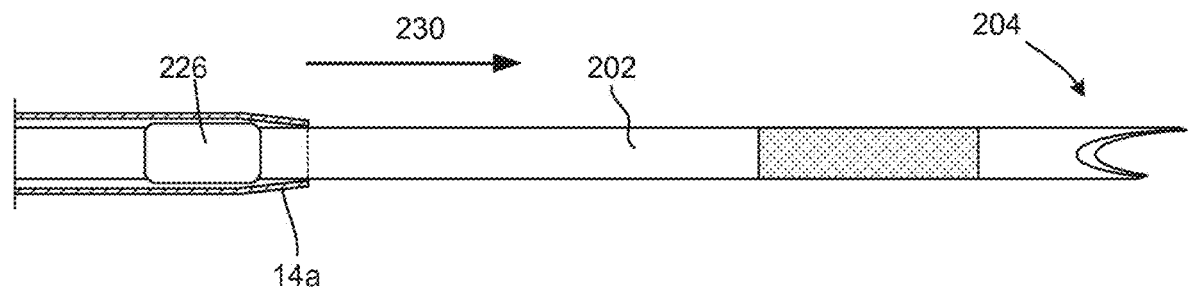
FIG. 18B is a side view, partly in section, of extension of the biopsy needle of FIG. 17 from the sheath of FIG. 13.

FIGS. 18A and 18B are side views, partly in section, of storage and extension of the biopsy needle 200 of FIG. 17 within the sheath 14 of the delivery system of FIG. 13. Referring to FIG. 18A, the needle 200 is shown loaded within the sheath 14 with the device handle in the fully retracted position and ready for extension into a target site for sample collection. In this instance, the distal end 204 of the needle 200 lies proximal to the distal tapered end 14a of the sheath 14. FIG. 18B illustrates the position of the needle 200 and needle collet 226 relative the sheath 14 when the needle transitions to a fully extended position, as indicated by arrow 230. In the fully extended position, the needle collet 226 remains housed inside sheath 14, proximal to the tapered distal tip, thereby preventing the needle 200 from extending past a set distance from the sheath 14.

It is important that the needle 200 can be passed through an internal diameter of a sheath 14 of the delivery device without catching on an internal wall of same, particularly during tissue collection procedures or needle exchanges. As the needle advances, the heel of the back-cut grind 218 on the first tip portion 206, for example, may come in contact with the internal diameter of the sheath 14 and reduce the friction between the distal end 204 of the needle 200, particularly the point 208 of the first tip portion 206, and the sheath 14. In this way, the needle 200 can be smoothly tracked through the sheath to exit the end of the sheath.

Figure 19A:
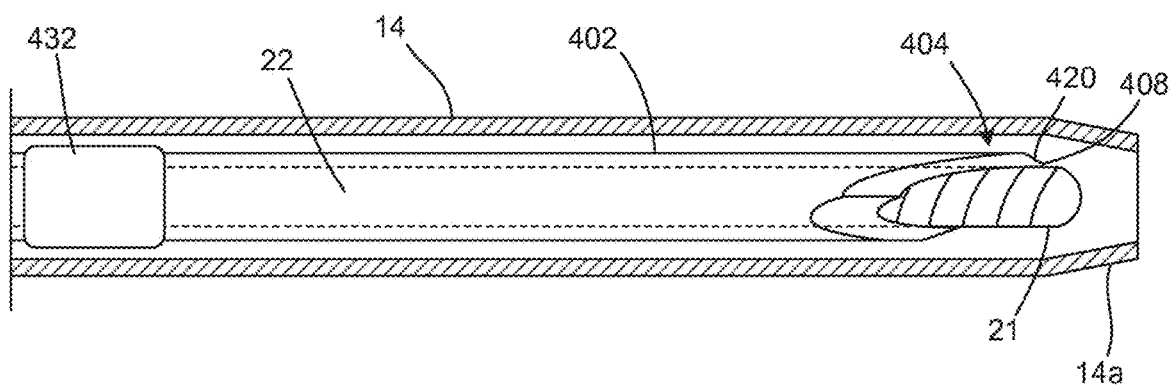
FIG. 19A is a side view, partly in section, of storage of the biopsy needle of FIG. 8 within the sheath of FIG. 13 showing the stylet shaft within the biopsy needle.
Figure 19B:
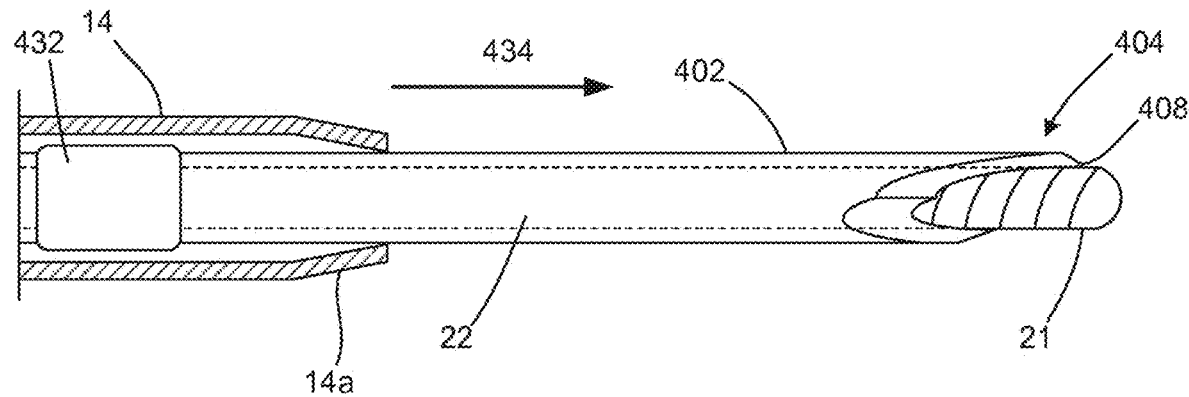
FIG. 19B is a side view, partly in section, of extension of the biopsy needle and stylet shaft from the sheath.
Figure 19C:
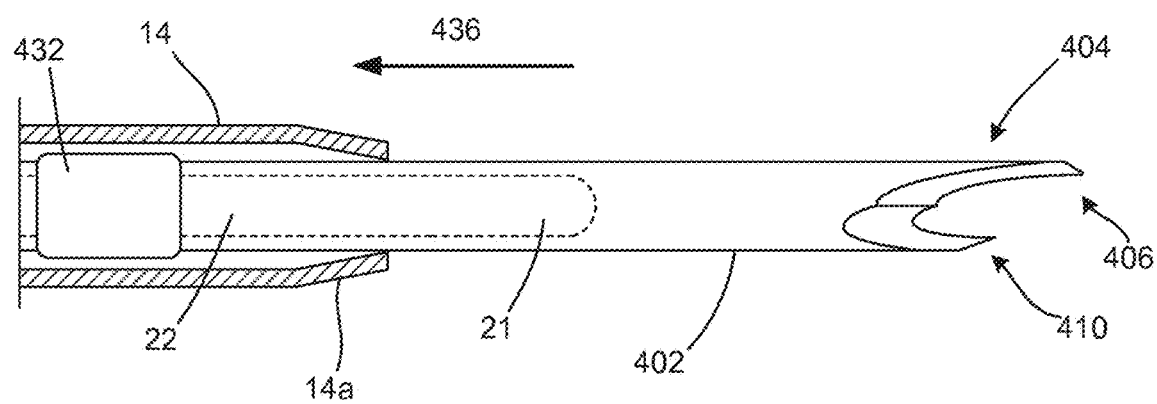
FIG. 19C is a side view, partly in section, of withdrawal of the stylet shaft from within at least the distal end of the biopsy needle to expose the first and second tip portions for sample tissue collection.

FIGS. 19A-19C are side views, partly in section, of the storage of needle 400 within the sheath 14 and extension of the needle 400 from the sheath 14 during a tissue collection procedure. In this embodiment, a stylet shaft 22 is shown positioned within the lumen 403 of the needle 400. The inclusion of the stylet shaft 22 within the lumen 403 of the needle 400 may be advantageous during both storage of the needle 400 as well as extension of the needle 400, as will be described in greater detail herein. As shown, the needle 400 may further include a needle collet 432 coupled to a portion of the needle body 402. The needle collet 432 is similarly configured as needle collet 226, previously described herein, and further functions in a similar manner. It should be noted that needle body 402 may further include one or more portions having echogenically enhanced regions, as previously described herein.

Referring to FIG. 19A, the needle 400 is shown loaded within the sheath 14 with the device handle in the fully retracted position and ready for extension into a target site for sample collection. In this instance, the distal end 404 of the needle 400 lies proximal to the distal tapered end 14a of the sheath 14. Further, the stylet shaft 22 is positioned within the lumen of the needle body 402. As generally understood, the stylet 22 may include, but is not limited to, a removable coaxial thin wire configured to be passed within the lumen 403 of the needle body 402. The stylet 22 may provide rigidity and stability to the needle 400 as well as the sheath 14, particularly when manipulating the sheath 14 and needle 400 (e.g., maneuvering of the sheath 14 or needle 400 to a desired site for tissue collection). Accordingly, the stylet 22 can be manufactured from a variety of metallic based materials, including, but not limited to, nitinol, cobalt chrome, stainless steel, a metal alloy, combinations thereof, or Polymeric Based materials including, but not limited to poly-ether-ether ketone, polyamide, poyethersulfone, polyurethane, ether block amide copolymers, polyacetal, polytetrafluoroethylene and/or derivatives thereof.

The stylet 22 is configured to further aid in the smooth passage of the needle 400 within the sheath 14, particularly during extension of the needle 400 from the sheath 14. FIG. 19B illustrates the position of the needle 400, stylet 22, and needle collet 432 relative the sheath 14 when the needle 400 transitions to an extended position, as indicated by arrow 434. In the an extended position, the needle collet 432 remains housed inside sheath 14 and is sized so as to prevent the needle 400 from extending past a set distance from the sheath 14. Furthermore, when the stylet 22 is in a loaded position, a distal end 21 of the stylet 22 is positioned at least flush with the distal end 404 (e.g., distal end 21 is positioned at or extending past the penetrating tip 408 of the leading first tip portion 406) so as to essentially prevent inadvertent catching of the penetrating tip 408 on the distal tapered end 14a of the sheath 14 during movement of the distal end 404 of the needle 400 through the distal tapered end 14a of the sheath 14. Additionally, as the needle 400 advances, the heel of the back-cut bevel grind 420 on the leading first tip portion 406, for example, may come in contact with the internal diameter of the sheath 14 and reduce the friction between the distal end 404 of the needle 400, particularly the penetrating tip 408 of the leading first tip portion 406, and the sheath 14. In this way, the needle 400 can be smoothly tracked through the sheath 14 to exit the distal tapered end 14a.

Furthermore, the stylet may be configured to protect the needle 400 from damage or inadvertent collection of a tissue sample. For example, as shown in FIG. 19B, once the distal end 404 of the needle 400 is extended from the sheath 14, the stylet 22 can remain in a loaded position (e.g., distal end 21 of the stylet 22 is positioned at or extending past the penetrating tip 408 of the leading first tip portion 406) until the clinician desires to begin tissue collection. In the illustrated embodiment, the distal end 21 of the stylet 22 is shown as having a rounded or blunt tip, so as to prevent puncturing of tissue. Accordingly, when in the loaded position, the stylet 22 prevents puncturing, excision, and subsequent collection of tissue within the needle 400. As shown in FIG. 19C, a clinician may subsequently withdraw the stylet 22 from the distal end 404 of the needle 400, as indicated by arrow 436, so as to expose the first and second tip portions 406, 410 for subsequent tissue collection. The stylet 22 may be moved to the loaded position at any time so as to prevent undesired tissue collection.

It should be noted that, in other embodiments, the stylet 22 may be used to initially puncture or penetrate a tissue to be collected. For example, in some embodiments, the distal end 21 of the stylet 22 may have a trocar pointed tip or other tip geometries configured to facilitate the introduction of the needle 400 into a tissue mass. Accordingly, the stylet 22 may be configured to aid the needle 400 in initially penetrating a tissue site, and, upon withdrawal of the stylet 22, the needle 400 is then configured to collect tissue upon further advancement into the tissue.

Figure 20:
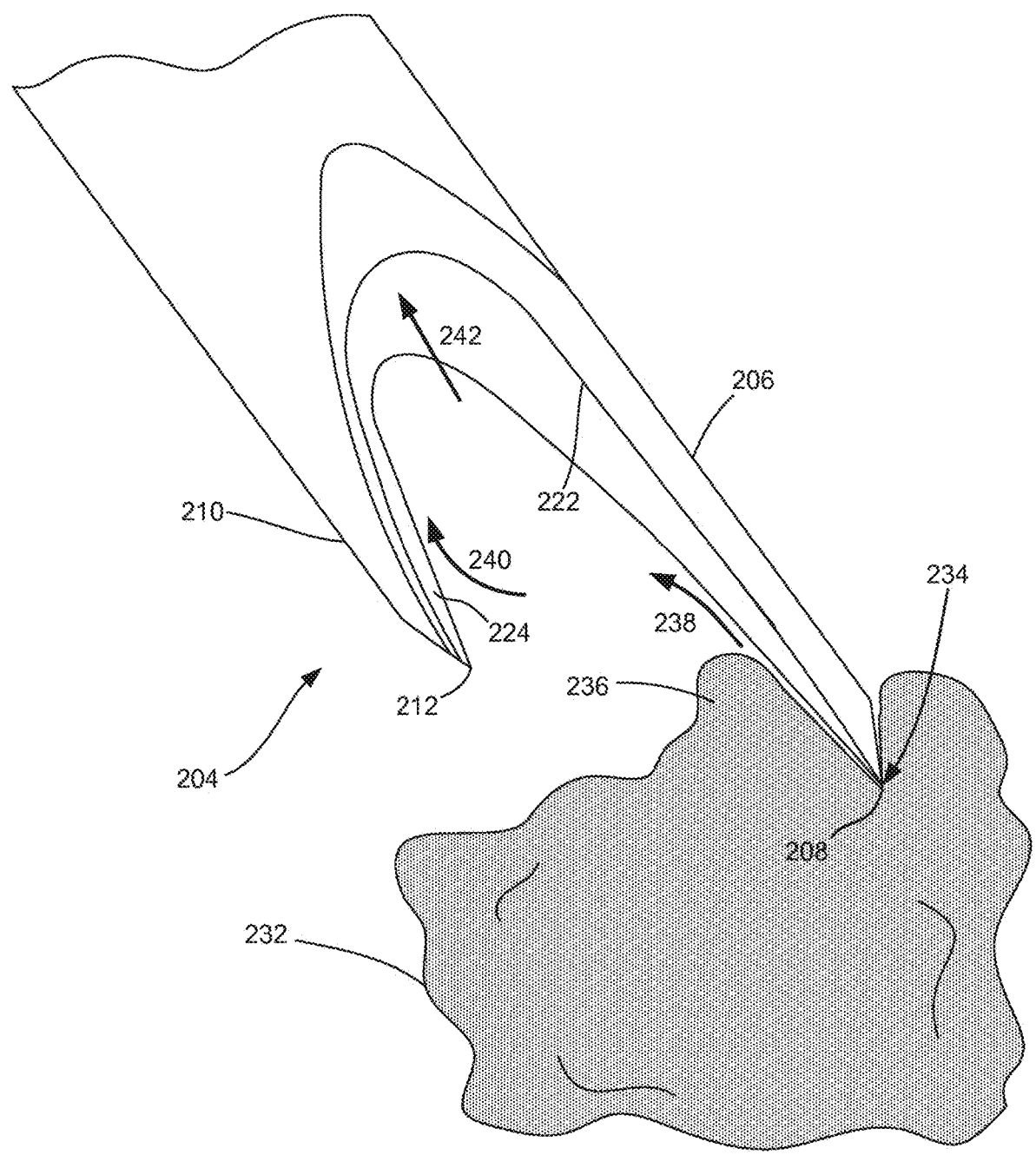
FIG. 20 is a perspective view illustrating the initiation of sample tissue collection with a biopsy needle consistent with the present disclosure.

FIG. 20 is a perspective view illustrating the initiation of sample tissue collection with biopsy needle 200. It should be noted that biopsy needle 400 is configured to collect sample tissue in a similar manner as biopsy needle 200, described in greater detail herein. Accordingly, the following description of sample tissue collection is not to be limited to biopsy needle 200. As shown, the needle 200 may be extended from the sheath 14 when delivered to a target site. An operator (e.g., physician or other trained medical personnel) may then advance the distal end 204 of the needle 200 towards the target tissue 232 to be sampled (with or without the assistance of use of ultrasound techniques). As shown, because the first tip portion 206 extends further than the second tip portion 210, the point 208 of the first tip portion 206 is configured to make initial contact and engage the tissue 232, as indicated by arrow 234. The first tip portion 206 is configured to pierce the tissue 232 and further direct a tissue sample 236 in a direction towards the lumen 203, as indicated by arrow 238. As the needle is forced further into the target tissue 232, the second tip portion 210, which is set back from the first tip portion 206, is configured to catch and grab additional tissue that may have otherwise deflected off of the first tip portion 206 and may have missed the lumen 203 entirely, as is the case with some current needle tip designs. For example, as tissue is excised by the cutting edge 222 after initial puncture by the point 208 of the first tip portion 206, the excised tissue may curl away from the first tip portion 206. The second tip portion 210 is then configured to catch and collect the deflected excised tissue, as indicated by arrow 240, and further pierce the target tissue 232, thereby guiding a tissue sample 236 towards the lumen 203 and to be further excised by the cutting edge 222 upon contact therewith, as indicated by arrow 242. In this manner, a full core sample may be achieved. In one embodiment, a vacuum may be communicated from the proximal end to the distal end 204 through the lumen 203 so as to provide a suction force to the target tissue 232 and further assist in collection and harvesting of the tissue sample via aspiration.

While several embodiments of the present disclosure have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present disclosure. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present disclosure is/are used.

Those skilled in the art will recognize, or be able to ascertain using no more than routine experimentation, many equivalents to the specific embodiments of the disclosure described herein. It is, therefore, to be understood that the foregoing embodiments are presented by way of example only and that, within the scope of the appended claims and equivalents thereto, the disclosure may be practiced otherwise than as specifically described and claimed. The present disclosure is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified, unless clearly indicated to the contrary.

Reference throughout this specification to "one embodiment" or "an embodiment" means that a particular feature, structure, or characteristic described in connection with the embodiment is included in at least one embodiment. Thus, appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The terms and expressions which have been employed herein are used as terms of description and not of limitation, and there is no intention, in the use of such terms and expressions, of excluding any equivalents of the features shown and described (or portions thereof), and it is recognized that various modifications are possible within the scope of the claims. Accordingly, the claims are intended to cover all such equivalents.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:

1. A biopsy needle comprising:
an elongate tubular body having a longitudinal axis and comprising a lumen extending therethrough from an open proximal end to an open distal end of the body, the distal end comprising a first tip portion extending from the distal end and having a first length, a second tip portion extending from the distal end and having a second length that is less than the first length of the first tip portion,
wherein the first tip portion is formed from a first set of distinct angular bevel grinds oblique to the longitudinal axis of the body and the second tip portion is formed from a second set of distinct angular bevel grinds oblique to the longitudinal axis of the body, and
wherein the first set of angular bevel grinds comprises a first bevel grind converging with a second bevel grind to form a penetrating tip of the first tip portion and the second set of angular bevel grinds comprises a third bevel grind converging with a fourth bevel grind to form a penetrating tip of the second tip portion, wherein the first and third bevel grinds form a third tip portion and the second and fourth bevel grinds form a fourth tip portion.

2. The biopsy needle of claim 1, wherein the first and second tip portions are on opposing sides of the body.

3. The biopsy needle of claim 1, wherein the third and fourth tip portions are on opposing sides of the body.

4. The biopsy needle of claim 1, wherein the third and fourth tip portions are formed between the first and second tip portions.

5. The biopsy needle of claim 1, wherein the second bevel grind converges with the fourth bevel grind to form a penetrating tip of the fourth tip portion.

6. The biopsy needle of claim 1 wherein the first bevel grind converges with the third bevel grind to form a penetrating tip of the third tip portion.

7. The biopsy needle of claim 1, wherein a third length of the third tip portion and a fourth length of the fourth tip portion is less than the first length of the first tip portion and greater than the second length of the second tip portion.

8. The biopsy needle of claim 7, wherein the third length and the fourth length are equal.

9. The biopsy needle of claim 1, wherein the first set of angular bevel grinds comprises a back-cut bevel grind defining a substantially planar surface adjacent to the penetrating tip of the first tip portion and defining a back-cut angle relative to an outer surface of the body and oblique to the outer surface of the body and the first and second bevel grinds.

10. The biopsy needle of claim 1, wherein the second set of angular bevel grinds comprises a back-cut bevel grind defining a substantially planar surface adjacent to the penetrating tip of the second tip portion and defining a back-cut angle relative to an outer surface of the body and oblique to the outer surface of the body and the third and fourth bevel grinds.

* * * * *